US006821947B2

(12) United States Patent
Iozzo

(10) Patent No.: US 6,821,947 B2
(45) Date of Patent: Nov. 23, 2004

(54) ENDOREPELLIN: METHODS AND COMPOSITIONS FOR INHIBITING ANGIOGENESIS

(75) Inventor: Renato V. Iozzo, Gladwyne, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 10/006,011

(22) Filed: Dec. 4, 2001

(65) Prior Publication Data

US 2003/0104999 A1 Jun. 5, 2003

(51) Int. Cl.[7] .......................... A01N 37/18; C07K 1/100
(52) U.S. Cl. .......................................... 514/2; 530/350
(58) Field of Search .............................. 514/2; 530/350

(56) References Cited

U.S. PATENT DOCUMENTS 5,958,883 A * 9/1999 Snow
6,284,726 B1 9/2001 Colman et al. ................ 514/2

FOREIGN PATENT DOCUMENTS

WO    WO 99/06054    *  2/1999

OTHER PUBLICATIONS

Murdoch et al (J. Biol. Chem. 1992;267(12):8544–8557).*
Auerbach et al (Clinical Chemistry 2003 49(1):32–40).*
Reiger et al (Glossary of Genetics and Cytogenetics, Classical and Molecular, 4th Ed., Springer–Verlay, Berlin, 1976.*
Dermer (Bio/Technology 1994; 12:320).*
Freshney (Culture of Animal Cells, A Manual of Basic Techniques, Alan R. Liss, Inc., 1983, New York, p4).*
D. M. Noonan, et al. *J.Biol.Chem.* 266, 22939–22947 (1991).
P. Kallunki, et al. *J.Cell Biol.* 116, 559–571 (1992).
A. D. Murdoch, et al., *J.Biol.Chem.* 267, 8544–8557 (1992).
D. Aviezer, et al., *Cell* 79, 1005–1013 (1994).
J.M. Whitelock, et al., *J. Biol. Chem.* 271, 10079–10086 (1996).
M.A. Nugent, et al., *Proc. Natl. Acad. Sci. USA* 97, 6722–6727 (2000).
R. V. Iozzo, *J.Cell Biol.* 99, 403–417 (1984).
I. R. Cohen, et al., *Cancer Res.* 54, 5771–5774 (1994).
D. Aviezer, et al., *Mol. Cell. Biol.* 17, 1938–1946 (1997).
R. Adatia, et al., *Ann. Oncol.* 8, 1257–1261 (1997).
Sharma, B. et al., *J.Clin. Invest.* 102, 1599–1608 (1998).
M. Mongiat, et al., *J.Biol.Chem.* 275, 7095–7100 (2000).
S. Gauer, et al., *Eur.J.Cell Biol.* 70, 233–242 (1996).
J. M. Whitelock, et al., *Matrix Biol.* 18, 163–178 (1999).
M. S. O'Reilly, *Cell* 88, 277–285 (1997).
W. Halfter, et al., *J.Biol.Chem.* 273, 25404–25412 (1998).
J. Saarela, et al., *Am.J.Pathol.* 153, 611–626 (1998).
N. Yamaguchi, et al., *EMBO J.* 18, 4414–4423 (1999).
W. Risau, *Nature* 386, 671–674 (1997).
J. C. Brown, et al., *Eur.J.Biochem.* 250, 39–46 (1997).
T. Sasaki, et al., *EMBO J.* 17, 4249–4256 (1998).
T. Sasaki, et al., *J.Mol.Biol.* 301, 1179–1190 (2000).
Z. Chang, et al., *Am.J.Pathol.* 155, 71–76 (1999).
K. Lundmark, et al., *J.Cell.Physiol.* 188, 67–74 (2001).
M. Mathiak, et al., *Cancer Res.* 57, 2130–2136 (1997).
A. G. Marneros, et al., *Matrix Biol.* 20, 337–345 (2001).
J. Xu, et al., *J.Cell Biol.* 154, 1069–1079 (2001).
R. V. Iozzo, *J.Clin.Invest.* 108, 165–167 (2001).
O. Oda, et al., *Clin.Chim.Acta* 255, 119–132 (1996).
M. Mongiat, et al., *J.Biol.Chem.* 276, 10263–10271 (2001).

* cited by examiner

*Primary Examiner*—Gary Nickol
*Assistant Examiner*—Christopher Yaen
(74) *Attorney, Agent, or Firm*—Drinker Biddle & Reath LLP

(57) ABSTRACT

Angiogenesis is a highly regulated process, yet many diseases are driven by unregulated angiogenesis. For example, the growth and metastasis of tumors is dependent on the growth of new blood vessels, which nurture the tumor by providing not only a growth-conducive environment but also a route by which metastatic cells can escape. The present invention provides an angiogenesis inhibiting agent endorepellin, its fragments or derivatives, or analogs thereof, which inhibit angiogenesis. The invention disclosed herein provides a novel therapeutic approach to the treatment of tumors, and other angiogenesis-mediated diseases or conditions, by inhibiting the generation of new blood vessels. The present invention also provides anti-endorepellin, its fragments or derivatives, or analogs thereof, antibodies for the detection, diagnosis and monitoring of angiogenesis-mediated diseases or conditions.

3 Claims, 22 Drawing Sheets

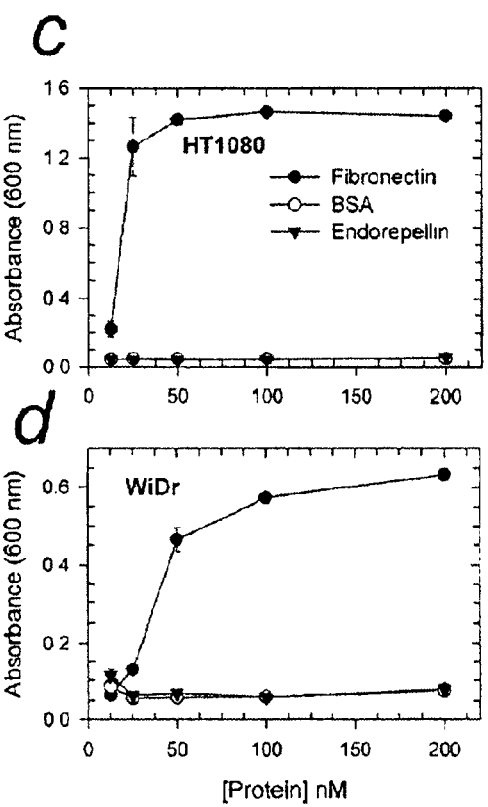
Fig. 5c-d

ENDOREPELLIN: METHODS AND COMPOSITIONS FOR INHIBITING ANGIOGENESIS

GOVERNMENT RIGHTS IN THE INVENTION

This invention was made with government support under grant CA47282 awarded by the NIH.

FIELD OF THE INVENTION

The present invention relates to the fields of tumor biology and molecular biology, and to a method of treating angiogenesis-related diseases or conditions and, more particularly, to the inhibition of neovascularization and tumor growth and metastasis in vivo.

BACKGROUND OF THE INVENTION

Perlecan is a modular proteoglycan that participates in the formation and maintenance of basement membranes in various organs (1,2). It is a major heparan sulfate proteoglycan (HSPG) secreted by endothelial cells and is a potent inhibitor of smooth muscle cell proliferation, a biological function mediated by perlecan's block of fibroblast growth factor 2 (FGF2) activity (13) and Oct-1 gene expression (14). Perlecan has been shown to play a critical role in regulating the vascular response to injury in vivo (17).

Angiogenesis is one of the most important events in tumor progression and is greatly influenced by cell-matrix interactions taking place at the surface of the endothelial cells and at the tumor-matrix boundaries (31). HSPGs act as depots for pro- and anti-angiogenic factors and, in concert with members of the FGF and vascular endothelial growth factor (VEGF) families and their receptors, modulate various aspects of angiogenesis (9). Interestingly, various angiogenesis inhibitors have been found to be proteolytically-processed forms of basement membrane collagens types IV, XV and XVIII, the latter two being chondroitin and HSPGs, respectively (32).

The invention presented herein describes a potent inhibitor of angiogenesis: the carboxyl terminus domain, domain V, of perlecan. This fragment, "endorepellin," inhibits angiogenesis and is active at nanomolar concentrations. Endorepellin interferes with endothelial cells' adhesive properties for various substrata, including, but not limited to, fibronectin and fibrillar collagen. Endorepellin, thus, represents a novel anti-angiogenic tool for the treatment of diseases or conditions associated with movement, migration and adhesion of cells, including diseases that involve angiogenesis such as, but not limited to, tumor metastasis and growth. The present invention provides endorepellin, analogs and fragments thereof, for use in inhibiting angiogenesis.

Abbreviations

"HSPG" means "heparan sulfate proteoglycans"

"HUVEC" means "human umbilical vein endothelial cells"

"CAM" means "chicken chorioallantoic membrane

"FGF" means "fibroblast growth factor"

"VEGF" means "vascular endothelial cell growth factor"

"LG" means "laminin-type G"

"EG" means "epidermal growth factor-like"

Definitions

"patient" as used herein can be one of many different species, including but not limited to, mammalian, bovine, ovine, porcine, equine, rodent and human.

"analog" as used herein is a derivative or modification of the native sequence. One skilled in the art may prepare such analogs wherein the native sequence is modified by resultant single or multiple amino acid substitutions, additions or deletions. All such modifications resulting in a derivative of endorepellin are included within the scope of the invention, provided that the molecule retains angiogenesis-inhibiting activity.

"substantial sequence homology" means at least approximately 60% homology between the amino acid residue sequence in the endorepellin analog or derivative sequence and that of endorepellin sequence.

"anti-angiogenesis activity" and "angiogenesis-inhibiting activity" refers to the ability of a molecule to inhibit the growth of blood vessels.

"angiogenesis-mediated disease" refers to the unregulated growth of new blood vessels that causes a disease or exacerbates an existing condition.

DESCRIPTION OF THE DRAWINGS

FIG. 1. Perlecan domain V (endorepellin) binds to the anti-angiogenic factor endostatin.

FIG. 2. Endorepellin is a powerful anti-angiogenic factor.

FIG. 3. Endorepellin, but not endostatin, blocks endothelial tube formation induced by fibrillar collagen.

FIG. 4. Biological consequences of endostatin/endorepellin interaction. FIG. 4a is the summary of three independent experiments run in quadruplicates, mean ±SE. The values in FIG. 4b derive from an additional experiment run in quadruplicate, mean ±SE. Serum free medium (SFM).

FIG. 5. Endorepellin is counter-adhesive for endothelial, fibrosarcoma and colon carcinoma cells. FIG. 5c and FIG. 5d, Adhesion assays for HT1080 fibrosarcoma and WiDr colon carcinoma cells, respectively, on fibronectin (★), BSA (†), or endorepellin (θ) substrata. The conditions are identical to those described in panel a. The values represent the mean ±SE (n=4).

DESCRIPTION OF THE INVENTION

Figure 1A:
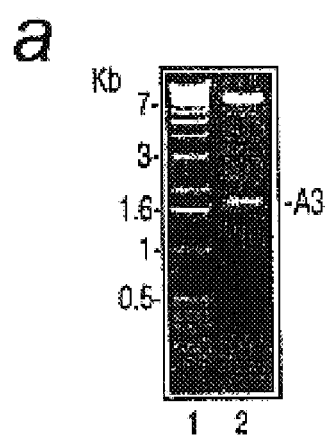
FIG. 1a, Agarose gel showing the 1.7 kb cDNA strongly interacting with endorepellin, obtained from the BgIII digestion of clone A3. Complete sequence of A3 clone revealed the C terminus of type XVIII collagen.
Figure 1B:
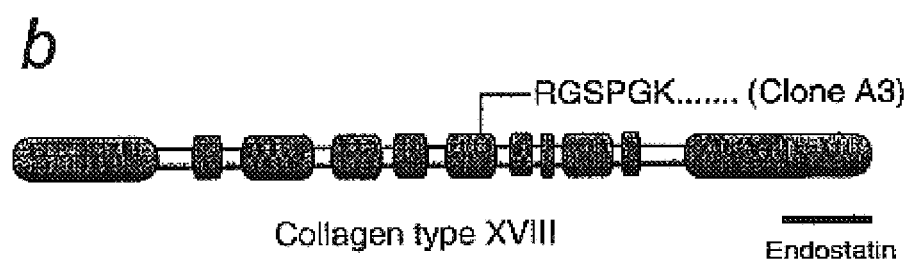
FIG. 1b, Schematic representation of the human α chain of type XVIII collagen. The triple-helical and non-triple helical domains are indicated by rods and blue boxes, respectively. The C-terminal endostatin fragment is highlighted in orange. The beginning of the clone A3 sequence is shown (NCBI accession # AF018082).

Angiogenesis, the process by which new blood vessels are formed, is essential for normal bodily activities including reproduction, development and wound repair. Although the process is not completely understood, angiogenesis is believed to involve a complex interplay of molecules, which regulate the growth of endothelial cells (the primary cells of capillary blood vessels). Under normal conditions, these molecules appear to maintain the microvasculature in a quiescent state (i.e. one of no capillary growth) for prolonged periods which may last for as long as weeks or, in some cases, decades. When necessary (such as during wound repair), these same cells can undergo rapid proliferation and turnover within a 5 day period.

Although angiogenesis is a highly regulated process under normal conditions, many diseases (characterized as angiogenic diseases) are driven by persistent unregulated angiogenesis. Otherwise stated, unregulated angiogenesis may either cause a particular disease directly or exasperbate an existing pathological condition. For example, growth and metastasis of solid tumors are dependent on angiogenesis. It has been shown, for example, that tumors which enlarge to greater than 2 mm must obtain their own blood supply and do so by inducing the growth of new capillary blood vessels. Neovascularization of a tumor enables the metastatic spread of tumor cells by providing a route of escape for the metastatic cells and nurturing the tumor by providing a growth-conducive environment. Another example is ocular neovascularization, a disease that has been implicated as the most common cause of blindness and dominates approximately twenty distinct eye diseases. In certain existing conditions, such as arthritis, newly formed capillary blood vessels invade the joints and destroy cartilage. In diabetes, new capillaries formed in the retina invade the vitreous, bleed, and cause blindness.

Many other diseases are driven by persistent unregulated angiogenesis. The diseases or conditions treatable by the present invention include, but are not limit to, primary tumor growth, tumor invasion or metastasis, hemangioma, leukemia, atherosclerosis, post-balloon angioplasty, myocardial angiogeneisis, plaque neovascularization, vascular restenosis, neointima formation following vascular trauma, vascular graft restenosis, fibrosis associated with a chronic inflammatory condition, lung fibrosis, chemotherapy-induced fibrosis, wound healing with scarring and fibrosis, psoriasis, deep venous thrombosis, corneal diseases, ovulation, menstration, placentation, or any other disease or condition which is mediated by angiogenesis. In addition, an important new medical method for birth control, wherein an effective amount of endorepellin is administered to a female such that uterine endometrial vascularization is inhibited and embryo implantation does not occur or is not sustained, is also contemplated by the present invention.

Angiogenesis Inhibitors

Angiogenesis inhibitors currently under development for use in treating angiogenic diseases have many disadvantages. Suramin, for example, is a potent angiogenesis inhibitor but causes severe systemic toxicity in humans at doses required for antitumor activity. Compounds such as retinoids, interferons and anti-estrogens are safe for human use but have weak anti-angiogenic effects. Thus, there is a need for compounds useful in treating angiogenic diseases in mammals. More specifically, there is a need for angiogenesis inhibitors which are safe for therapeutic use and which exhibit selective toxicity with respect to the pathological condition, such as by selectively inhibiting the proliferation of cancer cells while exhibiting no, or a low degree of toxicity to normal (ie. non-cancerous) cells. The present invention provides such a compound, endorepellin, to treat angiogenic-mediated diseases in mammals.

Furthermore, certain types of tumors are more amenable to therapy than others. Such tumors include, soft tissue tumors such as tumors of the blood. The reason for the increased efficacy in treatment regimens with respect to these tumors is their greater accessibility to chemotherapeutic agents. In contrast, it is much more difficult for most chemotherapeutic agents to reach all of the cells of a solid tumor mass.

Solid tumors rely on the generation of new blood vessels in order for the nutrients to reach the cells within the tumor. Thus, the present invention provides a novel therapeutic approach to the treatment of solid tumors wherein the generation of new blood vessels within the tumor, rather than the tumor cells themselves, is the target. This treatment is not likely to lead to the development of resistant tumor cells. Moreover, inhibition of angiogenesis leads to an amplification of the anti-tumor effect since many tumor cells rely on a single vessel for their nutrients.

Methods

Standard techniques are used for recombinant nucleic acid methods, polynucleotide synthesis, cell culture, and transgene incorporation (e.g., electroporation, microinjection, lipofection). The enzymatic reactions, oligonucleotide synthesis, and purification steps are performed according to the manufacturer's specifications. The techniques and procedures are performed according to conventional methods in the art and various general references that are provided throughout this document. The procedures therein are well known in the art, some of which are provided for the convenience of the reader.

Primary Culture and Cell Lines

Primary cultures of HUVECs are prepared from fresh umbilical cords and cultured on collagen-coated flasks in M199 or M200 medium supplemented with 10% FBS, 50 µg/ml heparan and endothelial cell growth supplement, isolated from bovine hypothalami. Only passages 4 to 8 are used. A431 squamous carcinoma cells, HT1080 fibrosarcoma, WiDr colon carcinoma, MCF7 breast carcinoma, and M2 mouse melanoma cells are obtained from American Type Culture Collection (Manassas, Va.).

Yeast Two-hybrid Screening and Co-immunoprecipitation

To reduce the number of false positives, the Matchmaker GAL4 two-hybrid system 3 (Clontech, Palo Alto, Calif.), which adopts three independent reporter genes for the selection, His, Ade and α or β-galactosidase, is used. A keratinocyte library constructed in the pACT2 vector is amplified and the plasmids are extracted employing the NucleoBond AX Giga plasmid purification kit (both the vector and kit are from Clontech). Endorepellin is subcloned into the pGBKT7 vector using PCR generated fragments as previously described (44), and is used as a bait to screen ~5×10$^6$ cDNAs. The yeast clones growing in selective medium are re-plated in quadruple minus plates containing X-gal. The plasmids from the blue colonies are isolated, expanded by subcloning in DH5α bacterial cells, and analyzed on agarose gels after restriction digestion with BglII. The inserts are identified by automatic sequencing.

Seven deletions of perlecan domain V are obtained by PCR, including suitable restriction sites to allow unidirectional ligation into the pGBKT7 vector (44). The various proteins are in vitro transcribed and translated in presence of [$^{35}$S]methionine (ICN Pharmaceuticals, Costa Mesa, Calif.) employing the TNT® reticulocyte lysate system (Promega, Madison, Wis.). One µg of the pGBKT7 or pGADT7 constructs is employed and the reactions are incubated for 90 min at 30° C. Aliquots are subjected to co-immunoprecipitation with affinity-purified, anti-hemagglutinin (αHA) rabbit polyclonal antibodies (Clontech). The immune-complexes are captured with protein A/G agarose beads (Pierce, Rockford, Ill.). The beads are washed three times with HNTG buffer (10 mM Hepes (pH 7.4), 150 mM NaCl, 0.1% triton X100, 10% glycerol, 200 mM Na$_2$VO$_4$, 20 mM NaF and an EDTA-free protease inhibitors cocktail (Roche Diagnostics GmbH, Mannheim, Germany). The bands are separated in polyacrylamide gels, fixed in the presence of AMPLIFY™ (Amersham Pharmacia Biotech, Uppsala, Sweden), dried under vacuum and exposed to KODAK films.

Expression and Purification of Recombinant Endorepellin

The pCEP-Pu vector bearing the sequence of the BM40 signal peptide is used to transfect by electroporation ~10$^7$ human kidney cells (293-EBNA) expressing the Epstein-Barr virus nuclear antigen (EBNA)-1. Mass cultures are selected in media containing 250 µg/ml G418 and 500 ng/ml puromycin. The confluent cells are allowed to express the recombinant protein in serum free for 48 hr. The conditioned media are concentrated in a dialysis bag with PEG and dialyzed in sonication buffer (12.5 mM Na$_3$PO$_4$, 75 mM NaCl, pH=8.0) and further purified employing the Ni-NTA resin and eluted with 250 mM imidazole. The fractions containing the recombinant protein are dialyzed against 10 mM Hepes, 150 mM NaCl and 2 mM EDTA and further concentrated. In all the purification steps phenylmethylsulfonyl fluoride (2 mM) and N-ethylmaleimide (2 mM) are the protease inhibitors. Using this procedure, 5–10 mg of endorepellin/L is routinely purified from conditioned medium. ELISA and immunoblotting with anti-domain V (16) or Penta-His (QIAGEN, Valenica, Calif.) monoclonal antibodies is performed as described before (24).

Endothelial Cell Migration, Tube Formation and Chorioallantoic Membrane (CAM) Assays A 48-well Boyden chamber (Neuroprobe Inc., Gaithersburg, Md.) is used for migration assays employing HUVECs. VEGF165 (R&D Systems, Minneapolis, Minn.) is used as a chemo-attractant in M199 (Life Technologies, Carlsbad, Calif.) containing 0.1% BSA. Cells migrated through eight-micron nucleopore polyvinylpyrrolidine-free polycarbonate filters (Corning, Cambridge, Mass.) precoated for 48 hr with 100 µg/ml collagen type I (Collaborative Biomedical Products, Bedford, Mass.) in 0.2 N acetic acid and air dried. The endothelial cells, trypsinized and re-suspended in M199 medium, are pre-incubated for 1 h with different concentrations of endorepellin and/or endostatin (Calbiochem-Novabiochem, San Diego, Calif.). The cells are allowed to migrate through the filter for 6 h at 37° C. with 5% CO$_2$. Every experiment is performed in quadruplicate, after each incubation, the filters are washed, fixed, stained with Diff-Quick stain (VWR Scientific Products, Bridgeport, N.J.), and counted in total using conventional microscopy.

For in vitro tube-like formation, 12-well cell culture dishes are coated with 100 µg/ml collagen type I in sterile 10 mM acetic acid. HUVECs seeded for 18 hr, and then covered with a second layer of collagen (41). Cultures are incubated until gels had solidified, typically 15–30 min, and then given 1 ml of media containing the various test agents and control substances.

For the CAM assays, fertilized White Leghorn chick eggs are incubated at 37° C. After three days of incubation, ~3 ml of albumin was removed to detach the CAM. A small square window is then opened in the eggshell, which is sealed with tape and the eggs are returned to the incubator. At day 9, a ~1 mm$^3$ Gelfoam sterile sponge Gelfoam (Pharmacia, North Peapak, N.J.) is placed on the chorioallantoic membranes and various test factors are applied including VEGF, endorepellin or buffer alone. The development of blood vessels is monitored by light microscopy up to 12 days.

Cell Adhesive and Counter-adhesive Assays

HUVECs and various tumor cells lines, including WiDr, A431, MCF7 and M2 cells, are tested for adhesion to various substrata including fibronectin, collagen type I, BSA, endorepellin or endostatin as plastic-immobilized substrata using dose-response profiles (coating concentrations of 10–180 nM). 5×10$^5$ cells are plated in quadruplicate wells and, after 1 hr of incubation, adherent cells are washed, fixed in 1% glutaraldehyde for 10 min, stained with crystal violet, lysed with 0.2% Triton X-100, and assayed by a colorimetric test (33). The crystal violet concentration, which is proportional to the cell number, is estimated at $A_{600}$.

The anti-adhesive assays are performed in a similar way. About 40 μg/ml fibronectin are used to coat individual plates. After blockage with 1% BSA, the cells are added to the wells in the presence of increasing concentration of endorepellin or endostatin. After 1 h of incubation, the wells are treated as above. Additional details are provided in the legends to the figures and in the methods (supra).

Endorepellin, Analogs and Fragements Thereof

Thus, the present invention contemplates amino acid residue sequences that have substantial sequence homology to endorepellin such that those sequences demonstrate like biological activity. It is well known in the art that modifications and changes can be made to a peptide without substantially altering the biological function of that peptide. For example, alterations to endorepellin peptide fragments may enhance the peptide's potency or stability to enzymatic breakdown. Such contemplated sequences include those analogous sequences characterized by a change in amino acid residue sequence or type wherein the change does not alter the fundamental nature and biological activity of the aforementioned endorepellin.

Generation of Antibodies to Endorepellin and Uses Thereof

According to the invention, endorepellin, its fragments or derivatives, or analogs thereof, may be used as an immunogen to generate antibodies that recognize such an immunogen. Such antibodies include but are not limited to polyclonal, monoclonal, chimeric, single chain, Fab fragments, and Fab expression library. In a specific embodiment, antibodies to endorepellin are produced.

Methods of producing endorepellin for generation of antibodies include, but are not limited to, recombinant DNA techniques, peptide synthesis wherein multiple fragments are synthesized and subsequently linked together to form the full length endorepellin, or proteolyic digestion of perlecan. These protocols are standard technology and well known to those of skill in the art.

Various procedures known in the art may be used for the production of polyclonal antibodies to endorepellin or derivatives or analogs thereof. For the production of antibody, various host animals can be immunized by injection with the native endorepellin, or a synthetic version, or derivative (e.g., fragment) thereof, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward an endorepellin sequence or analog thereof, any technique that provides for the production of antibody molecules by continuous cell lines in culture may be used. Examples of such techniques include, but are not limited to, the hybridoma, as well as the trioma technique, the human B-cell hybridoma technique, and the EBV-hybridoma technique to produce human monoclonal antibodies. In an additional embodiment of the invention, monoclonal antibodies can be produced in germ-free animals utilizing recent technology.

In the production of antibodies, screening for the desired antibody can be accomplished by techniques known in the art, such as, but not limited to, ELISA (enzyme-linked immunosorbent assay). For example, to select antibodies that recognize a specific domain of endorepellin, one may assay generated hybridomas for a product that binds to an endorepellin fragment containing such domain.

Diagnostic Uses of Antibodies

Anti-endorepellin antibodies may be generated (supra) and used to detect, prognose, diagnose, or monitor the treatment of angiogenesis-mediated diseases, such as cancer, by detecting the presence of endorepellin in patient samples. For detection of endorepellin sequences, a diagnostic kit of the present invention comprises, in one or more containers, an anti-endorepellin antibody that can be detectably labeled. In a different embodiment, the kit can comprise, in one or more containers, a labeled specific binding portion of an antibody. As used herein, the term "detectable label" refers to any label that provides directly or indirectly a detectable signal and includes, for example, enzymes, radiolabelled molecules, fluorescent molecules, particles, chemiluminesors, enzyme substrates or cofactors, enzyme inhibitors, or magnetic particles. Examples of enzymes useful as detectable labels in the present invention include, but are not limited to, alkaline phosphatase and horse-radish peroxidase. A variety of methods are available for linking the detectable labels to antibodies and include for example the use of a bifunctional agent, such as, 4,4'-difluoro-3,3'-dinitro-phenylsulfone, for attaching an enzyme, for example, horse radish peroxidase, to an antibody. The attached enzyme is then allowed to react with a substrate yielding a reaction product that is detectable. The present invention provides a method for detecting endorepellin in a patient sample, comprising, contacting the patient sample with an anti-endorepellin antibody under conditions such that immunospecific binding occurs, and detecting or measuring the amount of any immunospecific binding by the antibody.

Patient samples are any sample from a patient thought to contain endorepellin. Samples include, but are not limited to, peripheral blood or serum, urine, tissue sections, peritoneal fluid, cerebrospinal fluid, uterine fluid, mucus, etc.

Administration

This invention includes methods for inhibiting angiogenesis. By inhibiting angiogenesis, tumor metastasis is inhibited. In this method, a patient is administered an amount of endorepellin, its fragments or derivatives, or analogs thereof, effective to inhibit angiogenesis. The compound, or pharmaceutically acceptable salt thereof, is administered in the form of a pharmaceutical composition (infra).

Doses of the compounds include pharmaceutical dosage units comprising an effective amount of the peptide. By an effective amount is meant an amount sufficient to achieve a steady state concentration in vivo which results in a measurable reduction in any relevant parameter of disease, such as growth of primary or metastatic tumor, any accepted index of inflammatory reactivity, or a measurable prolongation of disease-free interval or survival.

In one embodiment, an effective dose is approximately between 10-fold and 100-fold higher than the 50% inhibitory concentration ($IC_{50}$) of the compound.

The amount of active compound to be administered depends on the precise peptide or derivative selected; the disease or condition; the route of administration; the health and weight of the recipient; the existence of other concurrent treatment; if any, the frequency of treatment, the nature of the effect desired, for example, inhibition of tumor metastasis; and the judgment of the skilled practitioner. The precise dose to be employed is decided according to the judgement of the practitioner and each patient's circumstances. The following are examples of such doses and is not meant to limit the invention in any way.

The proteins and protein fragments with endorepelliin activity are provided as isolated and substantially purified proteins and protein fragments in pharmaceutically acceptable formulations using formulation methods known to those of ordinary skill in the art. These formulations are administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the endorepellin, its fragments or derivatives, or analogs thereof, may be incorporated into biodegradable polymers allowing for sustained release of the compound, the polymers being implanted in the vicinity of where drug delivery is desired, for example, at the site of a tumor or implanted so that the endorepellin, its fragments, derivatives, or analogs thereof, is slowly released systemically. Osmotic minipumps also may be used to provide controlled delivery of high concentrations of endorepellin, its fragments, derivatives, or analogs thereof, through cannulae to the site of interest, such as directly into a metastatic growth or into the vascular supply to that tumor.

An exemplary dose for treating a patient with a tumor is an amount of up to about 100 milligrams of active compound per kilogram of body weight.

Typical single dosages of the peptide are between about 1 $\mu$g and about 100 mg/kg body weight. For topical administration, dosages are in the range of about 0.01–20% concentration of endorepellin, its fragments or derivatives, or analogs thereof. A total daily dosage in the range of about 10 milligrams to about 7 grams is exemplary for oral administration. The foregoing ranges are, however, exemplary, as the number of variables in regard to an individual treatment regimen is large, and considerable excursions from these recommended values are expected.

The therapeutic regimen with endorepellin, its fragments or derivatives, or analogs thereof, compounds of the invention produce an inhibitory effect on cell migration and invasion, on angiogenesis, on tumor metastasis and/or on inflammatory reactions in a patient having a disease or condition associated with undesired cell invasion, migration-induced proliferation, angiogenesis or metastasis (supra).

Endorepellin, its fragments, derivatives, or analogs thereof, of the present invention are useful for inhibiting angiogenesis when used alone or in combination with other compositions and procedures for the treatment of diseases. For example, a tumor may be treated conventionally with surgery, radiation or chemotherapy and endorepellin, or analogs or derivatives thereof, administration, either concurrently or subsequently, to extend the dormancy of micrometastases and to stabilize and inhibit the growth of any residual primary tumor.

Pharmaceutical Compositions

The present invention also provides pharmaceutical compositions. Such compositions comprise a therapeutically effective amount of endorepellin, its fragments, derivatives, or analogs thereof, and a pharmaceutically acceptable carrier or excipient. Such a carrier includes, but is not limited, to saline, buffered saline, dextrose, water, glycerol, ethanol, and combinations thereof. The carrier and composition are sterile. The formulation suits the mode of administration.

The composition, if desired, also can contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition also may include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The endorepellin, its fragments, derivatives, or analogs thereof, of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Results

Endostatin is a Novel Interacting Partner for Perlecan Domain V/Endorepellin

Figure 1C:
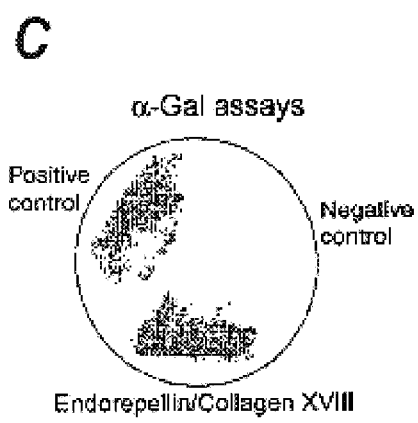
FIG. 1c, Growth and β-galactosidase activity triggered by the interaction of endorepellin with collagen type XVIII fragment compared to the positive (p53 and T-antigen) and negative control (lamin and T-antigen).

Using endorepellin as bait, a keratinocyte cDNA library is screened in the yeast two-hybrid system. One of the strongest interacting clones (clone A3) encoded the C-terminal portion of collagen type XVIII, containing the NC1 domain and the potent anti-angiogenic factor endostatin (FIGS. 1a and b). Since endostatin inhibits endothelial cell proliferation and effectively arrests the growth of several tumors (28), and because perlecan and endostatin co-localize in most tissues (29, 30), it is reasoned that an interaction between these two proteins could occur in vivo and could play a role in tumor progression. Therefore, the collagen fragment is sub-cloned into the pGADT7 vector, and the interaction with endorepellin is once more tested with the two-hybrid system on a one-to-one basis. The growth of the cells in quadruple minus medium is comparable to that of the positive control (pGBKT7-53/pGADT7-T), as well as the blue color generated by α-galactosidase expression (FIG. 1c).

Figure 1D:
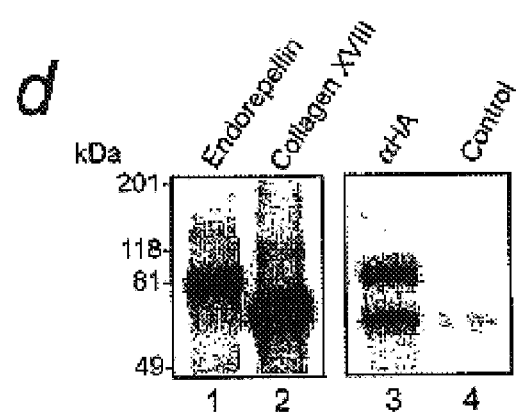
FIG. 1d, Co-immunoprecipitation of collagen XVIII (clone A3) and endorepellin following in vitro transcription/translation using [$^{35}$S]methionine as the labeled precursor. Endorepellin (lane 1) and collagen XVIII (lane 2) are mixed in equimolar amounts and co-immunoprecipitated with either anti-hemagglutinin (α-HA) (lane 3) or no antibody.
Figure 1E:
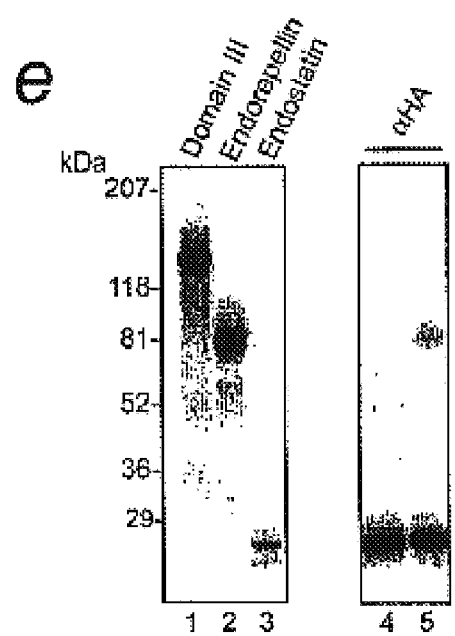
FIG. 1e, Co-immunoprecipitation of endostatin with endorepellin. Domain III (lane 1), endorepellin (lane 2) and endostatin (lane 3) were generated by in vitro transcription/translation using [$^{35}$S]methionine as the labeled precursor. Endostatin was mixed with either domain III (lane 4) or endorepellin (lane 5) and immunoprecipitated with anti-hemagglutinin (α-HA) antibody.

To corroborate the yeast interaction, collagen XVIII and endorepellin are transcribed and translated in vitro, resulting in the ~81 and ~65 kDa fragments, respectively (FIG. 1d). The two proteins are co-precipitated with an anti-hemagglunitin antibody which recognizes the oligopeptide epitope HA present at the C-terminus of collagen XVIII (FIG. 1d). To map the site of interaction, a deletion fragment of NC1 domain is cloned into pGADT7 containing only endostatin. The NC1 domain is then transcribed in vitro and translated resulting in a 23 kDa band (FIG. 1e, lane 3). As a further control, perlecan domain III is transcribed and translated, producing a ~130 kDa band (FIG. 1e, lane 1). The results show that only endorepellin interacts with endostatin (FIG. 1e, lane 5). In contrast, domain III does not bind to endostatin (lane 4). These experiments are repeated three times with comparable results.

Endostatin Interacts Specifically with the LG2 Module of Endorepellin

Figure 1F:
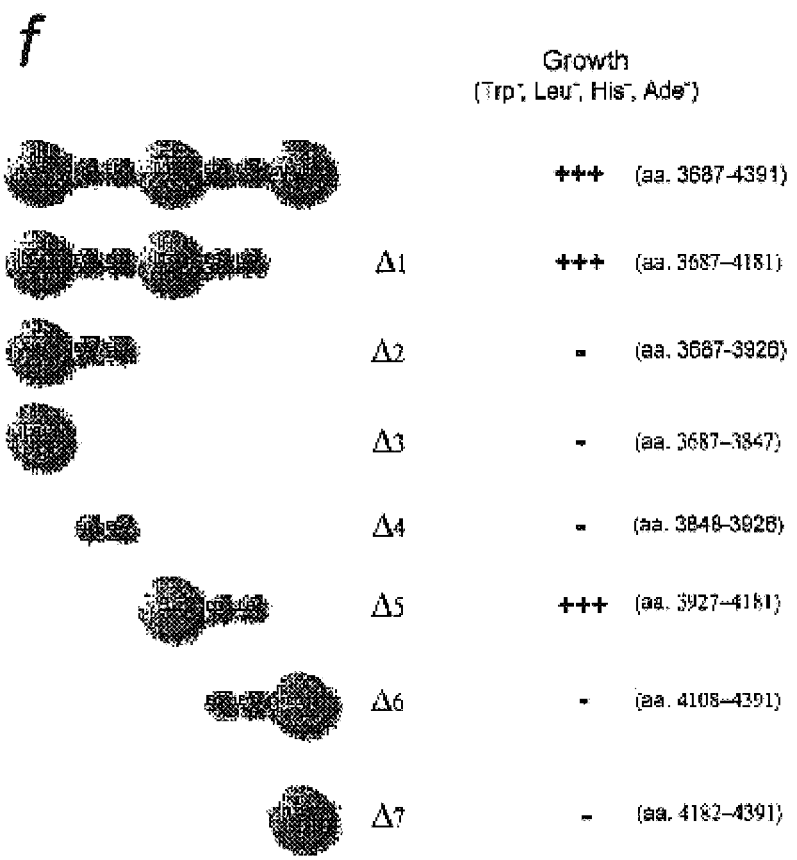
FIG. 1f, Schematic representation of domain V and various deletion mutants. Orange ovals indicate laminin-type G modules (LG), whereas blue rectangles indicate EGF-like (EG) modules. The growth is indicated by semi-quantitative assessment with maximal growth at +++. The numbers within parentheses designate the amino acid position based on the mature protein core.
Figure 1G:
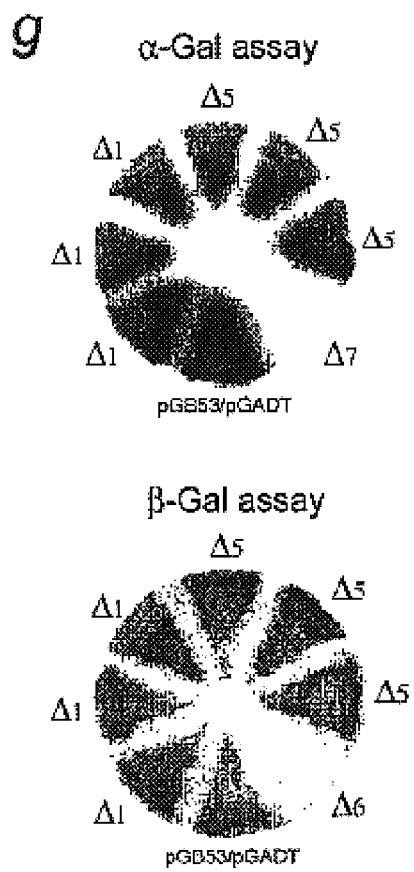
FIG. 1g, Representative α and β-galactosidase assays of various deletion mutants, as indicated; pGB53/pGADT was the positive control.

To establish the precise location of this interaction, seven deletion mutants of the domain V/endorepellin (SEQ ID NO:3) fragment of perlecan (SEQ ID NO:2) were generated, Δ1–Δ7 (SEQ ID NOS:4, 5, 6, 7, 8, 9, and 10) (FIG. 1f). This domain consists of three laminin type G (LG1–LG3) modules separated by four EGF-like (EG1–EG4) modules in an arrangement highly conserved across species (1). Robust growth in quadruple minus media is observed in cells co-transformed with full-length endorepellin (SEQ ID NO:3) and endorepellin with two deletions, Δ1 (SEQ ID NO:4) and Δ5 (SEQ ID NO:8), which contain the LG2 module (FIG. 1f). These results are corroborated by α- and β-galactosidase assays (FIG. 1g). Further support for a true protein/protein interaction is growth in amino acid-deficient media, transcription of LacZ (α- and β-galactosidase) under the control of distinct GAL4 upstream activating sequences, and the subsequent ability of the co-transformant yeast strains to express functional galactosidase activity. Thus, the LG2 module of endorepellin is the specific site of endostatin binding.

Recombinant Endorepellin is Anti-angiogenic

Figure 2A:
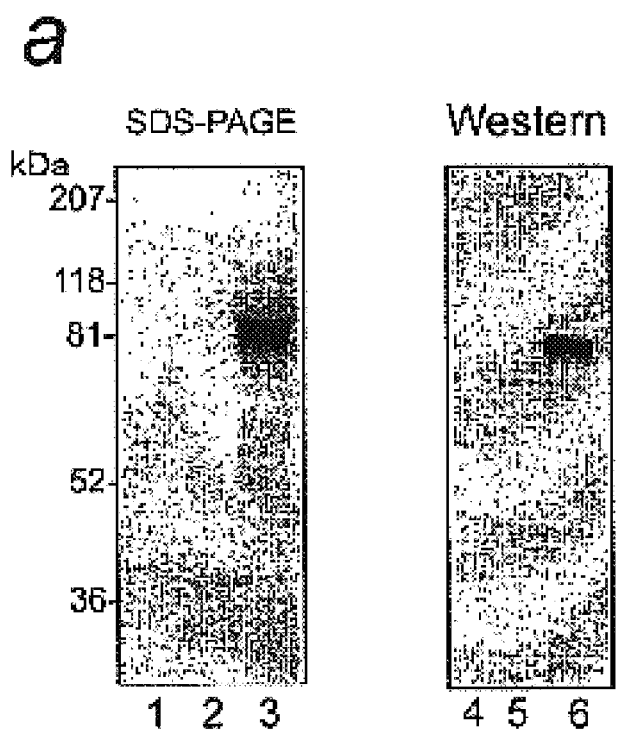
FIG. 2a, Purification of endorepellin from media conditioned by 293-EBNA cells expressing the 81 kDa endorepellin tagged with His6. Coumassie-stained SDS-PAGE (left) and Western immunoblotting with anti-His6 antibody (right) of negative control media (lanes 1 and 4), flow through (lanes 2 and 5), and 250 mM imidazole eluate (lanes 3 and 6).
Figure 2B:
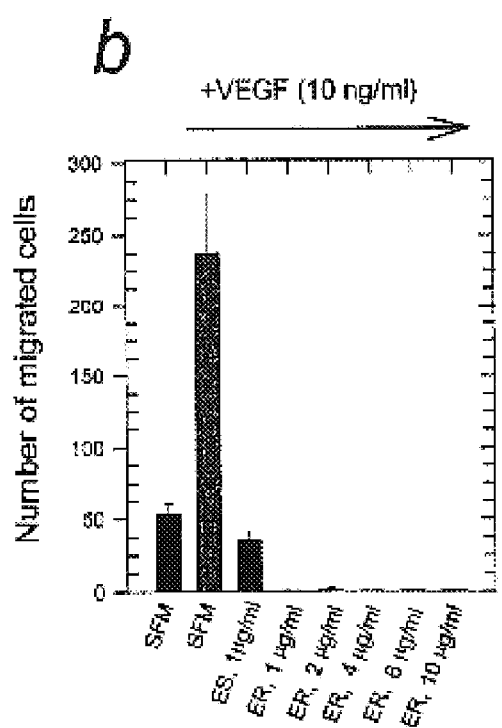
FIG. 2b and FIG. 2c, HUVEC migration assays through fibrillar collagen using 10 ng/ml VEGF as a chemotactic inducer and preincubation the HUVECs for 30 min with various concentrations of endostatin (ES) and endorepellin (ER). Serum free medium (SFM).
Figure 2C:
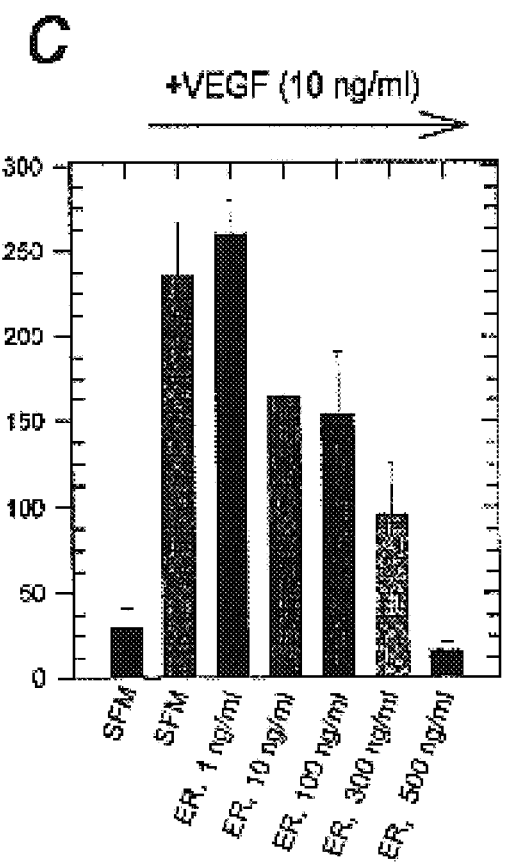

Human recombinant endorepellin, generated in 293-EBNA cells, migrated on SDS-PAGE as a single band of the predicted ~81 kDa. The identity of this recombinant protein is further confirmed by immunoblotting with anti-His6 antibody (FIG. 2a) and ELISA, using a specific monoclonal antibody against domain V (12). To test the biological properties of endorepellin, VEGF-induced migration of human umbilical vein endothelial cells (HUVEC) subcloned to passages 4–8 (31) is used. It is well established that the motility and vectorial migration of endothelial cells that occur with invasion is a fundamental component of angiogenesis (27,32). When VEGF is used in the lower chamber, there is a complete suppression of HUVEC migration through the membrane at 1–10 μg/ml (12–120 nM) endorepellin (FIG. 2b). Interestingly, endorepellin is more active than recombinant endostatin purified from *Pichia pastoris* yeast cells. Subsequent dilution experiments revealed that endorepellin is fully active at 0.5 μg/ml (6 nM) (FIG. 2c), with a calculated $IC_{50}$ of 1.2 nM (±0.1, n=11). In some preparations, endorepellin is active even at picomolar concentrations, similar to those reported for endostatin produced by 293-EBNA cells (31), the same cells used in this study. The experiments in FIGS. 2b and c are repeated eleven times with various preparations of endorepellin, and a marked suppression of HUVEC migration is consistently found. In contrast to endostatin, the migratory response is not dependent on preincubation of the endothelial cells with endorepellin. In experiments where endorepellin is placed in the lower chambers of the invasion assay, similar inhibition of VEGF-induced migration is found.

Figure 2D:
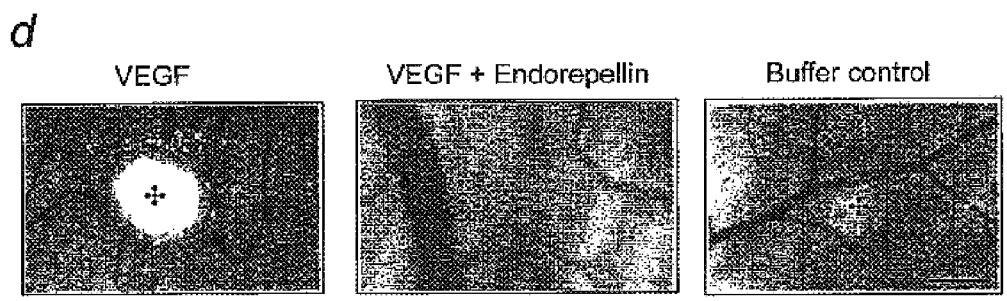
FIG. 2d, CAM assays three days after the application of sponges containing VEGF (1 ng), VEGF (1 ng)+endorepellin (400 ng), or buffer alone. Scale bar, 1 mm.

Endorepellin blocks the angiogenic activity of VEGF (FIG. 2d), as determined by the chicken chorioallantoic membrane (CAM) assay. Thus, HUVEC migration is inhibited, with the subsequent decrease in angiogenesis in vivo. In the presence of VEGF, the characteristic spoke wheel-like vessel formation is induced towards the sponge. In the presence of endorepellin, the vessel sprouts are markedly reduced to a level comparable to the negative control. These experiments are repeated several times with identical results.

Figure 3A:
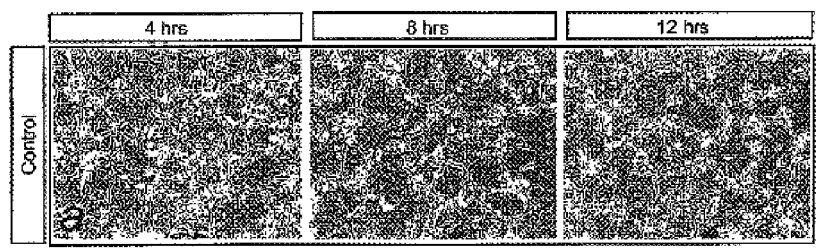
FIG. 3a, FIG. 3b, FIG. 3c, and FIG. 3d, Gallery of light micrographs capturing the time course production of HUVEC tube-like formation in fibrillar collagen containing either buffer (Control), endorepellin, endostatin, or both at the designated concentrations. In this assay, $4 \times 10^5$ cells are incubated for 24 hr and pictures are taken at various intervals as indicated in the top margins. Scale bar, 250 µm.
Figure 3B:
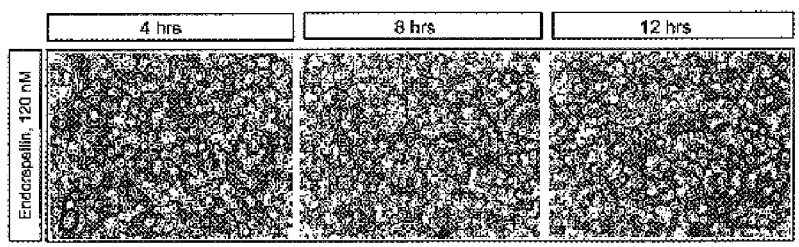
Figure 3C:
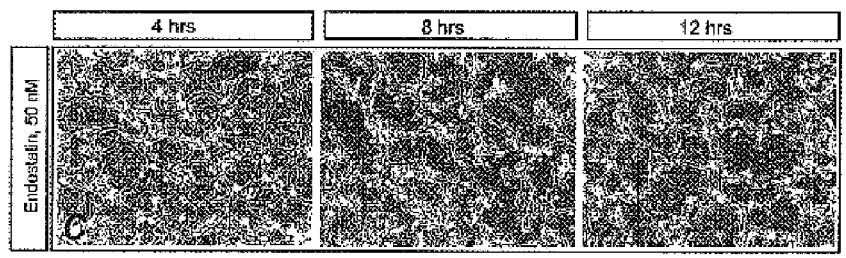
Figure 3D:
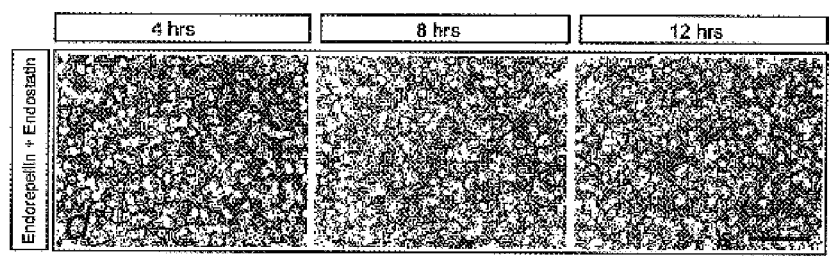

To further investigate the role of endorepellin in angiogenesis, HUVEC tube formation is utilized in a collagen matrix (33). The results show a capillary-like network formation in the control HUVECs (FIG. 3a), which is visible at 4 h and remained constant for up to 24 h. In contrast, endorepellin causes a complete block of tube-like formation (FIG. 3b), whereas no significant effects were obtained with endostatin (FIG. 3c). Surprisingly, endorepellin activity is counteracted by endostatin (FIG. 3d). It should be noted that the concentration of endorepellin used in these assays (μg/ml) is even lower than that used for the migration assays. In fact, while in the latter, full inhibition is detected at 300–500 ng endorepellin/$10^4$ HUVEC (30–50 pg/cell), in the former, full inhibition is achieved at 10 μg endorepellin/$4\times10^5$ HUVEC (25 pg/cell). Thus, the present invention reveals that endorepellin is a powerful blocker of angiogenesis in three independent assays commonly used to investigate angiogenesis.

Biological Effects of Endostatin/Endorepellin Interaction

Figure 4A:
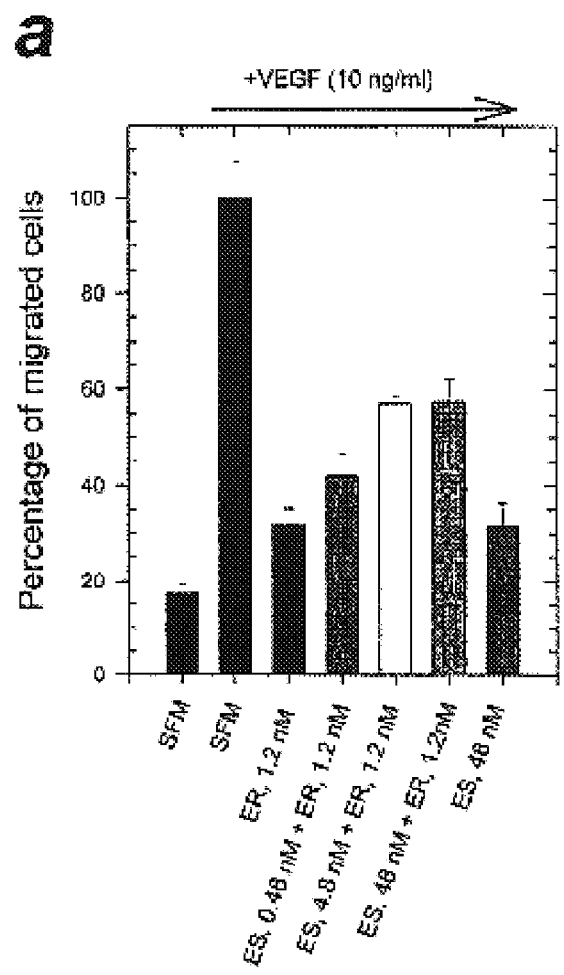
FIG. 4a and FIG. 4b, HUVEC migration assays through fibrillar collagen using 10 ng/ml VEGF as a chemotactic inducer and preincubation the HUVECs for 30 min with various concentrations of endostatin (ES), endorepellin (ER), or various combinations as indicated. The values are presented as the percentage of maximal stimulation induced by VEGF alone, arbitrarily set at 100%.
Figure 4B:
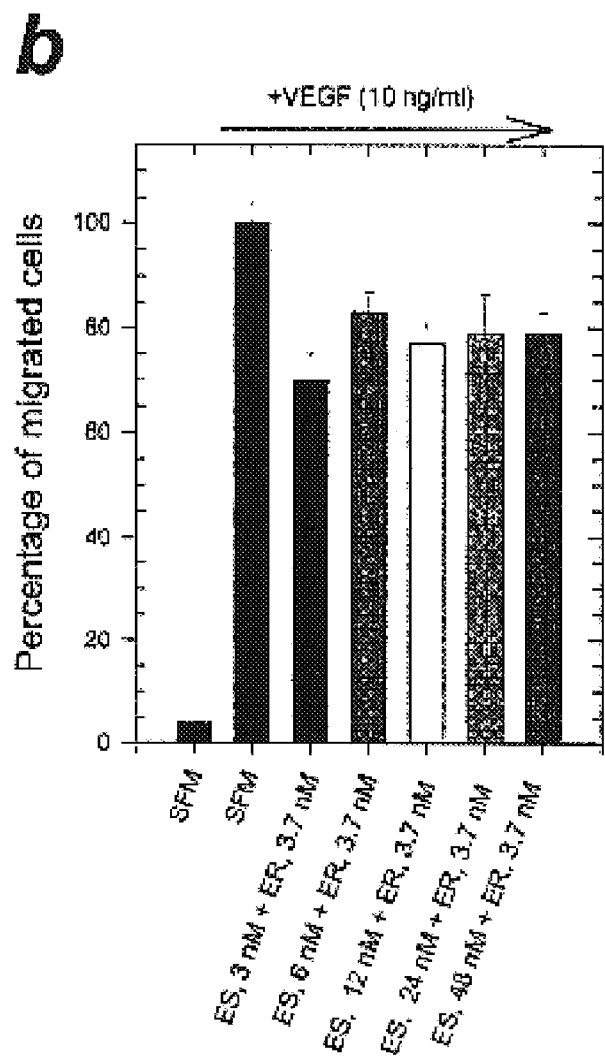

To further investigate the interaction between endostatin and endorepellin, several VEGF-induced HUVEC migration experiments are performed in which the amount of endorepellin is kept constant while the amount of endostatin is proportionally increased. Two concentrations of endorepellin are used, 1.2 and 3.7 nM (100 and 300 ng/ml, respectively), that give suboptimal and optimal inhibition of HUVEC migration. When endostatin and endorepellin are concurrently present, there is a significant and dose-dependent inhibition of their activity (FIGS. 4a and b). By plotting the percentage of migrated cells, derived from normalized data of five independent experiments against the increasing molar ratios of endostatin/endorepellin, it is evident that maximal inhibition is achieved at about 1:1 molar ratio; the inhibition subsequently declined (not shown). Thus, the interaction between endostatin and endorepellin leads to a marked attenuation of their anti-angiogenic activity.

Endorepellin has Counter-adhesive Properties for Endothelial Cells

Figure 5A:
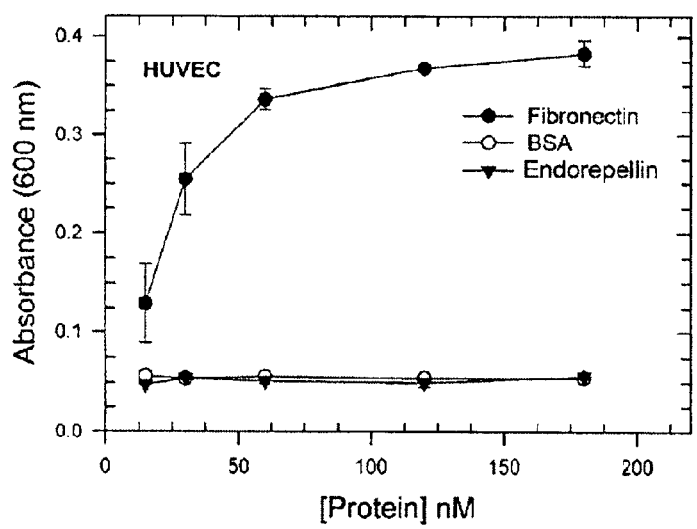
FIG. 5a, HUVEC adhesion to increasing concentrations of various substrata including fibronectin (★), BSA (†), or endorepellin (θ). For each point, $5 \times 10^4$ cells are seeded on the various substrata. After 1 h, adherent cells are washed, stained with crystal violet and solubilized in 0.1% Triton X-100, and absorbance monitored at 600 nm. The number of attached cells is proportional to the absorbance. About 80% of the total cells are attached in the plateau region of the fibronectin curve. The values represent the mean ±SE (n=4).
Figure 5B:
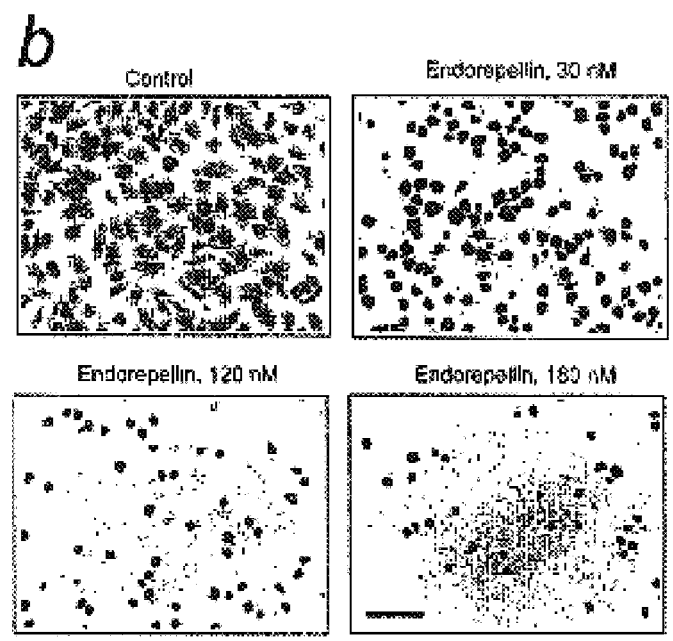
FIG. 5b, Gallery of light micrographs of crystal violet-stained HUVECs adhered to 50 nM fibronectin following incubation for 1 hr with endorepellin at the indicated concentrations. Scale bar, 125 µm.

A number of bioactive fragments of extracellular matrix proteins exhibit counter-adhesive activities, that is, they disrupt cell-matrix interactions (34). It has been previously shown that domain V of perlecan is adhesive for several cell lines vis á vis fibronectin, but not for others (35). To address this point, endorepellin is tested for its ability to mediate HUVEC adhesion. The result is a complete lack of HUVEC adhesion to either endorepellin or BSA, in contrast to a robust adhesion to fibronectin (FIG. 5a) or collagen type I. In competition experiments, in which HUVECs are challenged with increasing amounts of endorepellin, a progressive inhibition of HUVEC attachment occurs. Within minutes, the cells rounded up and began to detach in a dose-dependent manner (FIG. 5b). Several experiments on fibrillar collagen or plastic are performed and endorepellin consistently prevented HUVEC binding to either substratum, with $IC_{50}$ values of 5–20 nM. In contrast, endostatin does not show any interference with endothelial cell attachment to either fibronectin or collagen I.

Figure 5E:
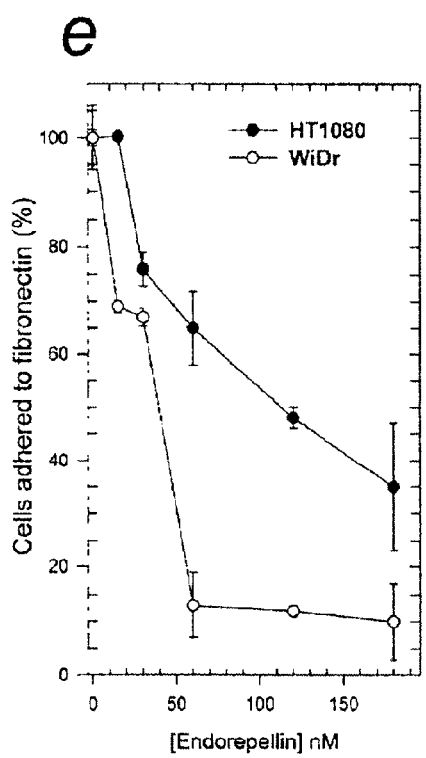
FIG. 5e and FIG. 5f, Displacement curves employing increasing concentration of either endorepellin or endostatin, respectively. The calculated $IC_{50}$ for HT1080 and WiDr was 110 and 40 nM, respectively. The values represent the mean ±SE (n=4).
Figure 5F:
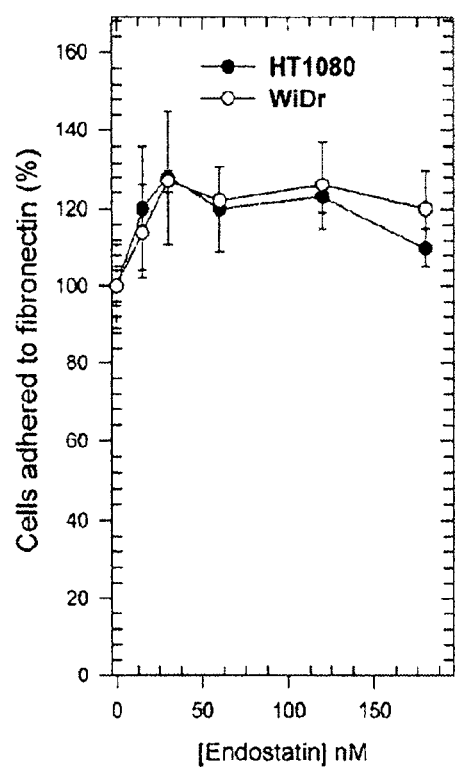

To verify that this anti-adhesive property of endorepellin is not limited to endothelial cells, HT1080 fibrosarcoma cells, which do not bind to murine domain V (35), and WiDr colon carcinoma cells (14) are tested. Endorepellin does not support adhesion of either HT1080 fibrosarcoma cells or WiDr colon carcinoma cells (FIGS. 5c and d). Moreover, the specificity of endorepellin counter-adhesive properties is demonstrated by the efficient displacement of HT1080 and WiDr attachment to fibronectin using increasing concentrations of recombinant endorepellin ($IC_{50}$ of 110 and 40 nM, respectively; FIG 5e). In contrast, endostatin does not significantly affect the adhesion of either cell line (FIG. 5f).

Adhesion assays also are performed using fibronectin and two concentrations of collagen type I with A431 squamous carcinoma cells, which were previously shown to adhere to murine domain V (58% of the values with a mean attachment value of 52±4% (Table 1) were obtained). Mouse M2 melanoma and human MCF7 breast carcinoma cells are also analyzed for adhesion in the presence of endorepellin. The resultant attachment values are <5% for mouse M2 melanoma cells and 50±7% for human MCF7 breast carcinoma cells (Table 1). Thus, endorepellin is a powerful anti-adhesive factor for endothelial cells and certain tumor cells.

Discussion

The present invention discloses screening, in vivo, for molecules that interact with the perlecan protein core. It is discovered that the cDNA encoding endostatin, the anti-angiogenic C-terminal fragment derived from collagen type XVIII (28), interacts strongly with the perlecan protein core. It previsously has been shown, using an in vitro cell-free system, that the entire perlecan binds to endostatin, presumably via the heparan sulfate chains (36,37). These results are confirmed herein. In addition, the present invention shows that a distinct subdomain of perlecan protein core binds specifically to endostatin.

Using a battery of deletion mutants, the precise binding site of endostatin to perlecan is mapped to the second laminin-like G (LG) domain of perlecan domain V. Since perlecan and type XVIII collagen/endostatin co-distribute in basement membranes (29, 30, 36) and endostatin binds in situ to vascular basement membranes independently of heparan sulfate (38), domain V is a likely binding site for endostatin in vivo.

Using HUVEC migration assays the present invention reveals that the interaction between endostatin and domain V counteracts the anti-angiogenic effects of endostatin. Since perlecan domain V itself is a powerful anti-angiogenic factor it is named herein "endorepellin". Endorepellin is active at nanomolar concentrations and is a potent inhibitor of angiogenesis in three independent assays commonly used to study angiogenesis: endothelial cell migration through fibrillar collagen, collagen-induced capillary-like formation, and growth of blood vessels in the chorioallantoic membrane. Interestingly, the action of endorepellin is as strong as endostatin in inhibiting HUVEC migration. Endorepellin interferes with the adhesive properties of endothelial cells for various substrata, including, but not limited to, fibronectin and fibrillar collagen, and also is anti-adhesive for certain tumor cells derived from colon, neuroectoderm or mesenchyme. This is in agreement with previous studies showing anti-adhesive properties for perlecan in hematopoietic (24), mesangial (25) and smooth muscle (39) cells, and a role for perlecan in the suppression of growth and invasion in fibrosarcoma cells (40). However, while endorepellin inhibits tube formation and prevents binding to fibronectin and other substrata, endostatin does not.

Powerful angiogenesis inhibitors are proteolytically-processed forms of basement membrane collagens types IV, XV and XVIII, the latter two being chondroitin and HSPGs, respectively (41). Moreover, proteolytic remodeling of the extracellular matrix can expose cryptic sites within collagen type IV that are required for angiogenesis in vivo (42). Thus, it is likely that perlecan undergoes a similar proteolytic processing in vivo, thereby liberating endorepellin.

The modular nature of the perlecan protein core is particularly well suited for selective proteolysis (12, 41, 43) and subsequent release of peptides with biological activity. There are two lines of evidence that support this scenario. First, in 293-EBNA cells a natural proteolytic cleavage of endorepellin of ~25 kDa is detected which binds to the Ni-NTA column and is also reactive with the anti-His6 antibody, indicating that it represents LG3. A similar size band previously was shown to represent a proteolytic fragment of murine domain V generated by cleavage just before the beginning of LG3 (9,35). This protease-sensitive region, which starts with the sequence DAPGQY (SEQ. ID. NO: 1), is completely conserved between mouse (3) and human (4), thus demonstrating that a specific cleavage of Asn-Asp bond (at position 3514/3515 and 4196/4197, for the mouse and human counterpart, respectively) had occurred near the N-terminus of LG3. Mutational analysis indicated that Asp but not Asn is crucial for processing of mouse endorepellin (44), possibly by a specific, yet to be discovered, Asp-N endoproteinase.

The second line of evidence is that an identical proteolytic fragment of ~25 kDa, cleaved at the same position as the mouse, was detected in the urine of patients with end-stage renal failure (45). This indicates that the LG3 module is present in human serum at relatively high concentrations since this LG3 was found at concentrations of ~10 mg/L of urine (45). Circulating forms of endorepellin may be involved in the homeostatic control of angiogenesis as proposed previously for endostatin, whose levels can reach 0.3 mg/L of blood (36).

Recent experimental tests on tumor-bearing animals are encouraging because protein-based inhibitors, such as endostatin, have three major advantages: 1) they can reduce the tumors to a bearable size, 2) they do not induce resistance, and 3) their toxicity is low (41). Endorepellin is a novel, natural inhibitor of angiogeneis and its use in cancer therapy has additional advantages insofar as endorepellin also exerts an anti-adhesive action on certain tumor cells. The invention disclosed herein presents a method wherein endorepellin inhibits angiogenesis and is used in the treatment of angiogenesis-mediated diseases (supra), such as cancer. Endorepellin also is used in conjunction with standard therapeutic agents to treat angiogenesis-dependent diseases, thereby enhancing the efficacy of current methodologies.

The foregoing descriptions of specific embodiments of the present invention have been presented for the purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention and various embodiments with various modifications as are suited to the particular use contemplated. It is intended that the scope of the invention be defined by the claims appended hereto and their equivalents.

References

1. Dunlevy, J. R. & Hassell, J. R. Heparan sulfate proteoglycans in basement membranes: Perlecan, agrin and collagen XVIII in Proteoglycans;Structure, biology and molecular interactions 275–326. Marcel Dekker, Inc., New York (2000).
2. Iozzo, R. V. Matrix proteoglycans: from molecular design to cellular function. Annu.Rev.Biochem. 67, 609–652 (1998).
3. Noonan, D. M. et al. The complete sequence of perlecan, a basement membrane heparan sulfate proteoglycan, reveals extensive similarity with laminin A chain, low density lipoprotein-receptor, and the neural cell adhesion molecule. J.Biol.Chem. 266, 22939–22947 (1991).

4. Kallunki, P. & Tryggvason, K. Human basement membrane heparan sulfate proteoglycan core protein: a 467-kD protein containing multiple domains resembling elements of low density lipoprotein receptor, laminin, neural cell adhesion molecules and epidermal growth factor. J.Cell Biol. 116, 559–571 (1992).
5. Murdoch, A. D., Dodge, G. R., Cohen, I., Tuan, R. S., & Iozzo, R. V. Primary structure of the human heparan sulfate proteoglycan from basement membrane (HSPG2/perlecan). A chimeric molecule with multiple domains homologous to the low density lipoprotein receptor, laminin, neural cell adhesion molecules, and epidermal growth factor. J.Biol.Chem. 267, 8544–8557 (1992).
6. Iozzo, R. V. & San Antonio, J. D. Heparan sulfate proteoglycans: heavy hitters in the angiogenesis arena. J.Clin.Invest. 108, 349–355 (2001).
7. Arikawa-Hirasawa, E., Watanabe, E., Takami, H., Hassell, J. R., & Yamada, Y. Perlecan is essential for cartilage and cephalic development. Nature Genet. 23, 354–358 (1999).
8. Costell, M. et al. Perlecan maintains the integrity of cartilage and some basement membranes. J.Cell Biol. 147, 1109–1122 (1999).
9. Nugent, M. A., Karnovsky, M. J., & Edelman, E. R. Vascular cell-derived heparan sulfate shows coupled inhibition of basic fibroblast growth factor binding and mitogenesis in vascular smooth muscle cells. Circ.Res. 73, 1051–1060 (1993).
10. Weiser, M. C. M., Grieshaber, N. A., Schwartz, P. E., & Majack, R. A. Perlecan regulates oct-1 gene expression in vascular smooth muscle cells. Mol.Biol.Cell 8, 999–1011 (1997).
11. Aviezer, D. et al. Perlecan, basal lamina proteoglycan, promotes basic fibroblast growth factor-receptor binding, mitogenesis, and angiogenesis. Cell 79, 1005–1013 (1994).
12. Whitelock, J. M., Murdoch, A. D., Iozzo, R. V., & Underwood, P. A. The degradation of human endothelial cell-derived perlecan and release of bound basic fibroblast growth factor by stromelysin, collagenase, plasmin and heparanases. J.Biol.Chem. 271, 10079–10086 (1996).
13. Nugent, M. A., Nugent, H. M., Iozzo, R. V., Sanchack, K., & Edelman, E. R. Perlecan is required to inhibit thrombosis after deep vascular injury and contributes to endothelial cell-mediated inhibition of intimal hyperplasia. Proc.Natl.Acad.Sci.USA 97, 6722–6727 (2000).
14. Iozzo, R. V. Biosynthesis of heparan sulfate proteoglycan by human colon carcinoma cells and its localization at the cell surface. J.Cell Biol. 99, 403–417 (1984).
15. Cohen, I. R. et al. Abnormal expression of perlecan proteoglycan in metastatic melanomas. Cancer Res. 54, 5771–5774 (1994).
16. Iozzo, R. V., Cohen, I. R., Grässel, S., & Murdoch, A. D. The biology of perlecan: the multifaceted heparan sulphate proteoglycan of basement membranes and pericellular matrices. Biochem.J. 302, 625–639 (1994).
17. Aviezer, D., Iozzo, R. V., Noonan, D. M., & Yayon, A. Suppression of autocrine and paracrine functions of basic fibroblast growth factor by stable expression of perlecan antisense cDNA. Mol.Cell.Biol. 17, 1938–1946 (1997).
18. Adatia, R. et al. Suppression of invasive behavior of melanoma cells by stable expression of anti-sense perlecan cDNA. Ann.Oncol. 8, 1257–1261 (1998).
19. Sharma, B. et al. Antisense targeting of perlecan blocks tumor growth and angiogenesis in vivo. J.Clin.Invest. 102, 1599–1608 (1998).
20. Mongiat, M. et al. The protein core of the proteoglycan perlecan binds specifically to fibroblast growth factor-7. J.Biol.Chem. 275, 7095–7100 (2000).
21. Ghiselli, G., Eichstetter, I., & Iozzo, R. V. A role for the perlecan protein core in the activation of the keratinocyte growth factor receptor. Biochem.J. 359, 153–163 (2001).
22. Timpl, R. Proteoglycans of basement membranes. Experientia 49, 417–428 (1993).
23. SundarRaj, N., Fite, D., Ledbetter, S., Chakravarti, L., & Hassell, J. R. Perlecan is a component of cartilage matrix and promotes chondrocyte attachment. J.Cell Sci. 108, 2663–2672 (1995).
24. Klein, G., Conzelmann, S., Beck, S., Timpl, R., & Müller, C. A. Perlecan in human bone marrow: a growth-factor presenting, but anti-adhesive, extracellular matrix component for hematopoietic cells. Matrix Biol. 14,457–465 (1995).
25. Gauer, S., Schulzelohoff, E., Schleicher, E., & Sterzel, R. B. Glomerular basement membrane-derived perlecan inhibits mesangial cell adhesion to fibronectin. Eur.J.Cell Biol. 70, 233–242 (1996).
26. Whitelock, J. M. et al. Human perlecan immunopurified from different endothelial cell sources has different adhesive properties for vascular cells. Matrix Biol. 18, 163–178 (1999).
27. Folkman, J. & D'Amore, P. A. Blood vessel formation: what is its molecular basis? Cell 87, 1153–1155 (1996).
28. O'Reilly, M. S. et al. Endostatin: an endogenous inhibitor of angiogenesis and tumor growth. Cell 88, 277–285 (1997).
29. Halfter, W., Dong, S., Schurer, B., & Cole, G. J. Collagen XVIII is a basement membrane heparan sulfate proteoglycan. J.Biol.Chem. 273, 25404–25412 (1998).
30. Saarela, J., Rehn, M., Oikarinen, A., Autio-Harmainen, H., & Pihlajaniemi, T. The short and long forms of type XVIII collagen show clear tissue specificities in their expression and location in basement membrane zones in humans. Am.J.Pathol. 153, 611–626 (1998).
31. Yamaguchi, N. et al. Endostatin inhibits VEGF-induced endothelial cell migration and tumor growth independently of zinc binding. EMBO J. 18, 4414–4423 (1999).
32. Risau, W. Mechanisms of angiogenesis. Nature 386, 671–674 (1997).
33. Montesano, R., Orci, L., & Vassalli, P. In vitro rapid organization of endothelial cells into capillary-like networks is promoted by collagen matrices. J.Cell Biol. 97, 1648–1652 (1983).
34. Sage, E. H. Pieces of eight-bioactive fragments of extracellular proteins as regulators of angiogenesis. Trends Cell Biol. 7, 182–186 (1997).
35. Brown, J. C., Sasaki, T., Göhring, W., Yamada, E., & Timpl, R. The C-terminal domain V of perlecan promotes 0.1 integrin-mediated cell adhesion, binds heparin, nidogen and fibulin-2 and can be modified by glycosaminoglycans. Eur.J.Biochem. 250, 39–46 (1997).
36. Sasaki, T. et al. Structure, function and tissue forms of the C-terminal globular domain of collagen XVIII containing the angiogenesis inhibitor endostatin. EMBO J. 17, 4249–4256 (1998).
37. Sasaki, T. et al. Endostatins derived from collagens XV and XVIII differ in structural and binding properties, tissue distribution and anti-angiogenic activity. J.Mol.Biol. 301, 1179–1190 (2000).
38. Chang, Z., Choon, A., & Friedl, A. Endostatin binds to blood vessels in situ independent of heparan sulfate and does not compete for fibroblast growth factor-2 binding. Am.J.Pathol. 155, 71–76 (2000).
39. Lundmark, K. et al. Perlecan inhibits smooth muscle cell adhesion to fibronectin: role of heparan sulfate. J.Cell. Physiol. 188, 67–74 (2001).
40. Mathiak, M., Yenisey, C., Grant, D. S., Sharma, B., & Iozzo, R. V. A role for perlecan in the suppression of growth and invasion in fibrosarcoma cells. Cancer Res. 57, 2130–2136 (1997).
41. Marneros, A. G. & Olsen, B. R. The role of collagen-derived proteolytic fragments in angiogenesis. Matrix Biol. 20, 337–345 (2001).

42. Xu, J. et al. Proteolytic exposure of a cryptic site within collagen type IV is required for angiogenesis and tumor growth in vivo. J.Cell Biol. 154, 1069–1079 (2001).
43. Iozzo, R. V. Heparan sulfate proteoglycans: intricate molecules with intriguing functions. J.Clin.Invest. 108, 165–167 (2001).
44. Friedrich, M. V. K., Göhring, W., Morgelin, M. B. A., David, G., & Timpl, R. Structural basis of glycosaminoglycan modification and of heterotypic interactions of perlecan domain V. J.Mol.Biol. 294, 259–270 (1999).
45. Oda, O. et al. Purification and characterization of perlecan fragment in urine of end-stage renal failure patients. Clin.Chim.Acta 255, 119–132 (1996).
46. Mongiat, M. et al. Fibroblast growth factor-binding protein is a novel partner for perlecan protein core. J.Biol.Chem. 276, 10263–10271 (2001).

What is claimed is:

1. A pharmaceutical composition, comprising:
   a) a polypeptide consisting of the amino acid sequence SEQ ID NO:3 or a fragment of said polypeptide which comprises the amino acid SEQ ID NO:10 and has agiogenesis-inhibiting activity; and
   b) a pharmaceutically acceptable carrier or excipient.

2. The pharmaceutical composition of claim 1, wherein said fragment consists of the amino acid sequence SEQ ID NO:9.

3. The pharmaceutical composition of claim 1, wherein said fragment consists of the amino acid sequence SEQ ID NO:10.

* * * * *

SEQUENCE LISTING

<160> NUMBER OF SEQ ID NOS: 10

<210> SEQ ID NO 1
<211> LENGTH: 6
<212> TYPE: PRT
<213> ORGANISM: human
<220> FEATURE:
<223> OTHER INFORMATION: frag. 3927-4181

<400> SEQUENCE: 1

Asp Ala Pro Gly Gln Tyr
1               5

<210> SEQ ID NO 2
<211> LENGTH: 4391
<212> TYPE: PRT
<213> ORGANISM: human

<400> SEQUENCE: 2

Met Gly Trp Arg Ala Pro Gly Ala Leu Leu Ala Leu Leu Leu His
1               5                   10                  15

Gly Arg Leu Leu Ala Val Thr His Gly Leu Arg Ala Tyr Asp Gly Leu
                20                  25                  30

Ser Leu Pro Glu Asp Ile Glu Thr Val Thr Ala Ser Gln Met Arg Trp
            35                  40                  45

Thr His Ser Tyr Leu Ser Asp Asp Glu Tyr Met Leu Ala Asp Ser Ile
        50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
                100                 105                 110

Glu Ala Val Val Asp Thr Leu Glu Ser Glu Tyr Leu Lys Ile Pro Gly
            115                 120                 125

Asp Gln Val Val Ser Val Val Phe Ile Lys Glu Leu Asp Gly Trp Val
        130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
                180                 185                 190

Pro Gln Phe Pro Arg Ala Cys Thr Glu Ala Glu Phe Ala Cys His Ser
            195                 200                 205

Tyr Asn Glu Cys Val Ala Leu Glu Tyr Arg Cys Asp Arg Arg Pro Asp
        210                 215                 220

Cys Arg Asp Met Ser Asp Glu Leu Asn Cys Glu Glu Pro Val Leu Gly

-continued

```
225                 230                 235                 240
Ile Ser Pro Thr Phe Ser Leu Leu Val Glu Thr Thr Ser Leu Pro Pro
                245                 250                 255
Arg Pro Glu Thr Thr Ile Met Arg Gln Pro Pro Val Thr His Ala Pro
            260                 265                 270
Gln Pro Leu Leu Pro Gly Ser Val Arg Pro Leu Pro Cys Gly Pro Gln
            275                 280                 285
Glu Ala Ala Cys Arg Asn Gly His Cys Ile Pro Arg Asp Tyr Leu Cys
        290                 295                 300
Asp Gly Gln Glu Asp Cys Glu Asp Gly Ser Asp Glu Leu Asp Cys Gly
305                 310                 315                 320
Pro Pro Pro Cys Glu Pro Asn Glu Phe Pro Cys Gly Asn Gly His
                325                 330                 335
Cys Ala Leu Lys Leu Trp Arg Cys Asp Gly Asp Phe Asp Cys Glu Asp
                340                 345                 350
Arg Thr Asp Glu Ala Asn Cys Pro Thr Lys Arg Pro Glu Glu Val Cys
            355                 360                 365
Gly Pro Thr Gln Phe Arg Cys Val Ser Thr Asn Met Cys Ile Pro Ala
370                 375                 380
Ser Phe His Cys Asp Glu Ser Asp Cys Pro Asp Arg Ser Asp Glu
385                 390                 395                 400
Phe Gly Cys Met Pro Pro Gln Val Val Thr Pro Arg Glu Ser Ile
                405                 410                 415
Gln Ala Ser Arg Gly Gln Thr Val Thr Phe Thr Cys Val Ala Ile Gly
            420                 425                 430
Val Pro Thr Pro Ile Ile Asn Trp Arg Leu Asn Trp Gly His Ile Pro
            435                 440                 445
Ser His Pro Arg Val Thr Val Thr Ser Glu Gly Gly Arg Gly Thr Leu
        450                 455                 460
Ile Ile Arg Asp Val Lys Glu Ser Asp Gln Gly Ala Tyr Thr Cys Glu
465                 470                 475                 480
Ala Met Asn Ala Arg Gly Met Val Phe Gly Ile Pro Asp Gly Val Leu
                485                 490                 495
Glu Leu Val Pro Gln Arg Gly Pro Cys Pro Asp Gly His Phe Tyr Leu
            500                 505                 510
Glu His Ser Ala Ala Cys Leu Pro Cys Phe Cys Phe Gly Ile Thr Ser
        515                 520                 525
Val Cys Gln Ser Thr Arg Arg Phe Arg Asp Gln Ile Arg Leu Arg Phe
    530                 535                 540
Asp Gln Pro Asp Asp Phe Lys Gly Val Asn Val Thr Met Pro Ala Gln
545                 550                 555                 560
Pro Gly Thr Pro Pro Leu Ser Ser Thr Gln Leu Gln Ile Asp Pro Ser
                565                 570                 575
Leu His Glu Phe Gln Leu Val Asp Leu Ser Arg Arg Phe Leu Val His
            580                 585                 590
Asp Ser Phe Trp Ala Leu Pro Glu Gln Phe Leu Gly Asn Lys Val Asp
            595                 600                 605
Ser Tyr Gly Gly Ser Leu Arg Tyr Asn Val Arg Tyr Glu Leu Ala Arg
        610                 615                 620
Gly Met Leu Glu Pro Val Gln Arg Pro Asp Val Val Leu Val Gly Ala
625                 630                 635                 640
Gly Tyr Arg Leu Leu Ser Arg Gly His Thr Pro Thr Gln Pro Gly Ala
                645                 650                 655
```

-continued

```
Leu Asn Gln Arg Gln Val Gln Phe Ser Glu Glu His Trp Val His Glu
            660                 665                 670
Ser Gly Arg Pro Val Gln Arg Ala Glu Leu Leu Gln Val Leu Gln Ser
        675                 680                 685
Leu Glu Ala Val Leu Ile Gln Thr Val Tyr Asn Thr Lys Met Ala Ser
    690                 695                 700
Val Gly Leu Ser Asp Ile Ala Met Asp Thr Thr Val Thr His Ala Thr
705                 710                 715                 720
Ser His Gly Arg Ala His Ser Val Glu Cys Arg Cys Pro Ile Gly
                725                 730                 735
Tyr Ser Gly Leu Ser Cys Glu Ser Cys Asp Ala His Phe Thr Arg Val
            740                 745                 750
Pro Gly Gly Pro Tyr Leu Gly Thr Cys Ser Gly Cys Ser Cys Asn Gly
        755                 760                 765
His Ala Ser Ser Cys Asp Pro Val Tyr Gly His Cys Leu Asn Cys Gln
    770                 775                 780
His Asn Thr Glu Gly Pro Gln Cys Asn Lys Cys Lys Ala Gly Phe Phe
785                 790                 795                 800
Gly Asp Ala Met Lys Ala Thr Ala Thr Ser Cys Arg Pro Cys Pro Cys
                805                 810                 815
Pro Tyr Ile Asp Ala Ser Arg Arg Phe Ser Asp Thr Cys Phe Leu Asp
            820                 825                 830
Thr Asp Gly Gln Ala Thr Cys Asp Ala Cys Ala Pro Gly Tyr Thr Gly
        835                 840                 845
Arg Arg Cys Glu Ser Cys Ala Pro Gly Tyr Glu Gly Asn Pro Ile Gln
    850                 855                 860
Pro Gly Gly Lys Cys Arg Pro Val Asn Gln Glu Ile Val Arg Cys Asp
865                 870                 875                 880
Glu Arg Gly Ser Met Gly Thr Ser Gly Glu Ala Cys Arg Cys Lys Asn
                885                 890                 895
Asn Val Val Gly Arg Leu Cys Asn Glu Cys Ala Asp Gly Ser Phe His
            900                 905                 910
Leu Ser Thr Arg Asn Pro Asp Gly Cys Leu Lys Cys Phe Cys Met Gly
        915                 920                 925
Val Ser Arg His Cys Thr Ser Ser Ser Trp Ser Arg Ala Gln Leu His
    930                 935                 940
Gly Ala Ser Glu Glu Pro Gly His Phe Ser Leu Thr Asn Ala Ala Ser
945                 950                 955                 960
Thr His Thr Thr Asn Glu Gly Ile Phe Ser Pro Thr Pro Gly Glu Leu
                965                 970                 975
Gly Phe Ser Ser Phe His Arg Leu Leu Ser Gly Pro Tyr Phe Trp Ser
            980                 985                 990
Leu Pro Ser Arg Phe Leu Gly Asp Lys Val Thr Ser Tyr Gly Gly Glu
        995                 1000                1005
Leu Arg Phe Thr Val Thr Gln Arg Ser Gln Pro Gly Ser Thr Pro Leu
    1010                1015                1020
His Gly Gln Pro Leu Val Val Leu Gln Gly Asn Asn Ile Ile Leu Glu
1025                1030                1035                1040
His His Val Ala Gln Glu Pro Ser Pro Gly Gln Pro Ser Thr Phe Ile
                1045                1050                1055
Val Pro Phe Arg Glu Gln Ala Trp Gln Arg Pro Asp Gly Gln Pro Ala
            1060                1065                1070
```

```
Thr Arg Glu His Leu Leu Met Ala Leu Ala Gly Ile Asp Thr Leu Leu
        1075                1080                1085

Ile Arg Ala Ser Tyr Ala Gln Gln Pro Ala Glu Ser Arg Val Ser Gly
        1090                1095                1100

Ile Ser Met Asp Val Ala Val Pro Glu Glu Thr Gly Gln Asp Pro Ala
1105                1110                1115                1120

Leu Glu Val Glu Gln Cys Ser Cys Pro Pro Gly Tyr Arg Gly Pro Ser
                1125                1130                1135

Cys Gln Asp Cys Asp Thr Gly Tyr Thr Arg Thr Pro Ser Gly Leu Tyr
            1140                1145                1150

Leu Gly Thr Cys Glu Arg Cys Ser Cys His Gly His Ser Glu Ala Cys
        1155                1160                1165

Glu Pro Glu Thr Gly Ala Cys Gln Gly Cys Gln His His Thr Glu Gly
        1170                1175                1180

Pro Arg Cys Glu Gln Cys Gln Pro Gly Tyr Tyr Gly Asp Ala Gln Arg
1185                1190                1195                1200

Gly Thr Pro Gln Asp Cys Gln Leu Cys Pro Cys Tyr Gly Asp Pro Ala
                1205                1210                1215

Ala Gly Gln Ala Ala His Thr Cys Phe Leu Asp Thr Asp Gly His Pro
        1220                1225                1230

Thr Cys Asp Ala Cys Ser Pro Gly His Ser Gly Arg His Cys Glu Arg
        1235                1240                1245

Cys Ala Pro Gly Tyr Tyr Gly Asn Pro Ser Gln Gly Gln Pro Cys Gln
1250                1255                1260

Arg Asp Ser Gln Val Pro Gly Pro Ile Gly Cys Asn Cys Asp Pro Gln
1265                1270                1275                1280

Gly Ser Val Ser Ser Gln Cys Asp Ala Ala Gly Gln Cys Gln Cys Lys
                1285                1290                1295

Ala Gln Val Glu Gly Leu Thr Cys Ser His Cys Arg Pro His His Phe
        1300                1305                1310

His Leu Ser Ala Ser Asn Pro Asp Gly Cys Leu Pro Cys Phe Cys Met
        1315                1320                1325

Gly Ile Thr Gln Gln Cys Ala Ser Ser Ala Tyr Thr Arg His Leu Ile
        1330                1335                1340

Ser Thr His Phe Ala Pro Gly Asp Phe Gln Gly Phe Ala Leu Val Asn
1345                1350                1355                1360

Pro Gln Arg Asn Ser Arg Leu Thr Gly Glu Phe Thr Val Glu Pro Val
                1365                1370                1375

Pro Glu Gly Ala Gln Leu Ser Phe Gly Asn Phe Ala Gln Leu Gly His
            1380                1385                1390

Glu Ser Phe Tyr Trp Gln Leu Pro Glu Thr Tyr Gln Gly Asp Lys Val
        1395                1400                1405

Ala Ala Tyr Gly Gly Lys Leu Arg Tyr Thr Leu Ser Tyr Thr Ala Gly
        1410                1415                1420

Pro Gln Gly Ser Pro Leu Ser Asp Pro Asp Val Gln Ile Thr Gly Asn
1425                1430                1435                1440

Asn Ile Met Leu Val Ala Ser Gln Pro Ala Leu Gln Gly Pro Glu Arg
                1445                1450                1455

Arg Ser Tyr Glu Ile Met Phe Arg Glu Glu Phe Trp Arg Arg Pro Asp
            1460                1465                1470

Gly Gln Pro Ala Thr Arg Glu His Leu Leu Met Ala Leu Ala Asp Leu
        1475                1480                1485

Asp Glu Leu Leu Ile Arg Ala Thr Phe Ser Ser Val Pro Leu Val Ala
```

-continued

```
           1490                1495                1500
Ser Ile Ser Ala Val Ser Leu Glu Val Ala Gln Pro Gly Pro Ser Asn
1505                1510                1515                1520

Arg Pro Arg Ala Leu Glu Val Glu Glu Cys Arg Cys Pro Pro Gly Tyr
                1525                1530                1535

Ile Gly Leu Ser Cys Gln Asp Cys Ala Pro Gly Tyr Thr Arg Thr Gly
                1540                1545                1550

Ser Gly Leu Tyr Leu Gly His Cys Glu Leu Cys Glu Cys Asn Gly His
                1555                1560                1565

Ser Asp Leu Cys His Pro Glu Thr Gly Ala Cys Ser Gln Cys Gln His
    1570                1575                1580

Asn Ala Ala Gly Glu Phe Cys Glu Leu Cys Ala Pro Gly Tyr Tyr Gly
1585                1590                1595                1600

Asp Ala Thr Ala Gly Thr Pro Glu Asp Cys Gln Pro Cys Ala Cys Pro
                1605                1610                1615

Leu Thr Asn Pro Glu Asn Met Phe Ser Arg Thr Cys Glu Ser Leu Gly
                1620                1625                1630

Ala Gly Gly Tyr Arg Cys Thr Ala Cys Glu Pro Gly Tyr Thr Gly Gln
                1635                1640                1645

Tyr Cys Glu Gln Cys Gly Pro Gly Tyr Val Gly Asn Pro Ser Val Gln
    1650                1655                1660

Gly Gly Gln Cys Leu Pro Glu Thr Asn Gln Ala Pro Leu Val Val Glu
1665                1670                1675                1680

Val His Pro Ala Arg Ser Ile Val Pro Gln Gly Gly Ser His Ser Leu
                1685                1690                1695

Arg Cys Gln Val Ser Gly Ser Pro Pro His Tyr Phe Tyr Trp Ser Arg
                1700                1705                1710

Glu Asp Gly Arg Pro Val Pro Ser Gly Thr Gln Gln Arg His Gln Gly
                1715                1720                1725

Ser Glu Leu His Phe Pro Ser Val Gln Pro Ser Asp Ala Gly Val Tyr
    1730                1735                1740

Ile Cys Thr Cys Arg Asn Leu His Gln Ser Asn Thr Ser Arg Ala Glu
1745                1750                1755                1760

Leu Leu Val Thr Glu Ala Pro Ser Lys Pro Ile Thr Val Thr Val Glu
                1765                1770                1775

Glu Gln Arg Ser Gln Ser Val Arg Pro Gly Ala Asp Val Thr Phe Ile
                1780                1785                1790

Cys Thr Ala Lys Ser Lys Ser Pro Ala Tyr Thr Leu Val Trp Thr Arg
                1795                1800                1805

Leu His Asn Gly Lys Leu Pro Thr Arg Ala Met Asp Phe Asn Gly Ile
    1810                1815                1820

Leu Thr Ile Arg Asn Val Gln Leu Ser Asp Ala Gly Thr Tyr Val Cys
1825                1830                1835                1840

Thr Gly Ser Asn Met Phe Ala Met Asp Gln Gly Thr Ala Thr Leu His
                1845                1850                1855

Val Gln Ala Ser Gly Thr Leu Ser Ala Pro Val Val Ser Ile His Pro
                1860                1865                1870

Pro Gln Leu Thr Val Gln Pro Gly Gln Leu Ala Glu Phe Arg Cys Ser
            1875                1880                1885

Ala Thr Gly Ser Pro Thr Pro Thr Leu Glu Trp Thr Gly Gly Pro Gly
    1890                1895                1900

Gly Gln Leu Pro Ala Lys Ala Gln Ile His Gly Gly Ile Leu Arg Leu
1905                1910                1915                1920
```

-continued

```
Pro Ala Val Glu Pro Thr Asp Gln Ala Gln Tyr Leu Cys Arg Ala His
            1925                1930                1935

Ser Ser Ala Gly Gln Gln Val Ala Arg Ala Val Leu His Val His Gly
            1940                1945                1950

Gly Gly Gly Pro Arg Val Gln Val Ser Pro Glu Arg Thr Gln Val His
            1955                1960                1965

Ala Gly Arg Thr Val Arg Leu Tyr Cys Arg Ala Gly Val Pro Ser
    1970                1975                1980

Ala Thr Ile Thr Trp Arg Lys Glu Gly Ser Leu Pro Pro Gln Ala
1985                1990                1995                2000

Arg Ser Glu Arg Thr Asp Ile Ala Thr Leu Leu Ile Pro Ala Ile Thr
                2005                2010                2015

Thr Ala Asp Ala Gly Phe Tyr Leu Cys Val Ala Thr Ser Pro Ala Gly
                2020                2025                2030

Thr Ala Gln Ala Arg Met Gln Val Val Val Leu Ser Ala Ser Asp Ala
            2035                2040                2045

Ser Pro Pro Gly Val Lys Ile Glu Ser Ser Ser Pro Ser Val Thr Glu
    2050                2055                2060

Gly Gln Thr Leu Asp Leu Asn Cys Val Val Ala Gly Ser Ala His Ala
2065                2070                2075                2080

Gln Val Thr Trp Tyr Arg Arg Gly Gly Ser Leu Pro Pro His Thr Gln
                2085                2090                2095

Val His Gly Ser Arg Leu Arg Leu Pro Gln Val Ser Pro Ala Asp Ser
        2100                2105                2110

Gly Glu Tyr Val Cys Arg Val Glu Asn Gly Ser Gly Pro Lys Glu Ala
            2115                2120                2125

Ser Ile Thr Val Ser Val Leu His Gly Thr His Ser Gly Pro Ser Tyr
    2130                2135                2140

Thr Pro Val Pro Gly Ser Thr Arg Pro Ile Arg Ile Glu Pro Ser Ser
2145                2150                2155                2160

Ser His Val Ala Glu Gly Gln Thr Leu Asp Leu Asn Cys Val Val Pro
                2165                2170                2175

Gly Gln Ala His Ala Gln Val Thr Trp His Lys Arg Gly Gly Ser Leu
            2180                2185                2190

Pro Ala Arg His Gln Thr His Gly Ser Leu Leu Arg Leu His Gln Val
            2195                2200                2205

Thr Pro Ala Asp Ser Gly Glu Tyr Val Cys His Val Val Gly Thr Ser
    2210                2215                2220

Gly Pro Leu Glu Ala Ser Val Leu Val Thr Ile Glu Ala Ser Val Ile
2225                2230                2235                2240

Pro Gly Pro Ile Pro Pro Val Arg Ile Glu Ser Ser Ser Ser Thr Val
                2245                2250                2255

Ala Glu Gly Gln Thr Leu Asp Leu Ser Cys Val Val Ala Gly Gln Ala
            2260                2265                2270

His Ala Gln Val Thr Trp Tyr Lys Arg Gly Gly Ser Leu Pro Ala Arg
            2275                2280                2285

His Gln Val Arg Gly Ser Arg Leu Tyr Ile Phe Gln Ala Ser Pro Ala
    2290                2295                2300

Asp Ala Gly Gln Tyr Val Cys Arg Ala Ser Asn Gly Met Glu Ala Ser
2305                2310                2315                2320

Ile Thr Val Thr Val Thr Gly Thr Gln Gly Ala Asn Leu Ala Tyr Pro
                2325                2330                2335
```

-continued

Ala Gly Ser Thr Gln Pro Ile Arg Ile Glu Pro Ser Ser Gln Val
         2340                2345            2350

Ala Glu Gly Gln Thr Leu Asp Leu Asn Cys Val Val Pro Gly Gln Ser
         2355                2360            2365

His Ala Gln Val Thr Trp His Lys Arg Gly Gly Ser Leu Pro Val Arg
         2370                2375            2380

His Gln Thr His Gly Ser Leu Leu Arg Leu Tyr Gln Ala Ser Pro Ala
2385             2390                2395                2400

Asp Ser Gly Glu Tyr Val Cys Arg Val Leu Gly Ser Ser Val Pro Leu
         2405                2410            2415

Glu Ala Ser Val Leu Val Thr Ile Glu Pro Ala Gly Ser Val Pro Ala
         2420                2425            2430

Leu Gly Val Thr Pro Thr Val Arg Ile Glu Ser Ser Ser Ser Gln Val
         2435                2440            2445

Ala Glu Gly Gln Thr Leu Asp Leu Asn Cys Leu Val Ala Gly Gln Ala
         2450                2455            2460

His Ala Gln Val Thr Trp His Lys Arg Gly Gly Ser Leu Pro Ala Arg
2465             2470                2475                2480

His Gln Val His Gly Ser Arg Leu Arg Leu Leu Gln Val Thr Pro Ala
         2485                2490            2495

Asp Ser Gly Glu Tyr Val Cys Arg Val Val Gly Ser Ser Gly Thr Gln
         2500                2505            2510

Glu Ala Ser Val Leu Val Thr Ile Gln Gln Arg Leu Ser Gly Ser His
         2515                2520            2525

Ser Gln Gly Val Ala Tyr Pro Val Arg Ile Glu Ser Ser Ser Ala Ser
         2530                2535            2540

Leu Ala Asn Gly His Thr Leu Asp Leu Asn Cys Leu Val Ala Ser Gln
2545             2550                2555                2560

Ala Pro His Thr Ile Thr Trp Tyr Lys Arg Gly Gly Ser Leu Pro Ser
         2565                2570            2575

Arg His Gln Ile Val Gly Ser Arg Leu Arg Ile Pro Gln Val Thr Pro
         2580                2585            2590

Ala Asp Ser Gly Glu Tyr Val Cys His Val Ser Asn Gly Ala Gly Ser
         2595                2600            2605

Arg Glu Thr Ser Leu Ile Val Thr Ile Gln Gly Ser Gly Ser Ser His
         2610                2615            2620

Val Pro Ser Val Ser Pro Ile Arg Ile Glu Ser Ser Ser Pro Thr
2625             2630                2635                2640

Val Val Glu Gly Gln Thr Leu Asp Leu Asn Cys Val Val Ala Arg Gln
         2645                2650            2655

Pro Gln Ala Ile Ile Thr Trp Tyr Lys Arg Gly Gly Ser Leu Pro Ser
         2660                2665            2670

Arg His Gln Thr His Gly Ser His Leu Arg Leu His Gln Met Ser Val
         2675                2680            2685

Ala Asp Ser Gly Glu Tyr Val Cys Arg Ala Asn Asn Asn Ile Asp Ala
         2690                2695            2700

Leu Glu Ala Ser Ile Val Ile Ser Val Ser Pro Ser Ala Gly Ser Pro
2705             2710                2715                2720

Ser Ala Pro Gly Ser Ser Met Pro Ile Arg Ile Glu Ser Ser Ser Ser
         2725                2730            2735

His Val Ala Glu Gly Glu Thr Leu Asp Leu Asn Cys Val Val Pro Gly
         2740                2745            2750

Gln Ala His Ala Gln Val Thr Trp His Lys Arg Gly Gly Ser Leu Pro

-continued

```
            2755                2760                2765
Ser His His Gln Thr Arg Gly Ser Arg Leu Arg Leu His His Val Ser
            2770                2775                2780
Pro Ala Asp Ser Gly Glu Tyr Val Cys Arg Val Met Gly Ser Ser Gly
2785                2790                2795                2800
Pro Leu Glu Ala Ser Val Leu Val Thr Ile Glu Ala Ser Gly Ser Ser
                2805                2810                2815
Ala Val His Val Pro Ala Pro Gly Gly Ala Pro Pro Ile Arg Ile Glu
            2820                2825                2830
Pro Ser Ser Arg Val Ala Glu Gly Gln Thr Leu Asp Leu Lys Cys
            2835                2840                2845
Val Val Pro Gly Gln Ala His Ala Gln Val Thr Trp His Lys Arg Gly
            2850                2855                2860
Gly Asn Leu Pro Ala Arg His Gln Val His Gly Pro Leu Leu Arg Leu
2865                2870                2875                2880
Asn Gln Val Ser Pro Ala Asp Ser Gly Glu Tyr Ser Cys Gln Val Thr
                2885                2890                2895
Gly Ser Ser Gly Thr Leu Glu Ala Ser Val Leu Val Thr Ile Glu Pro
            2900                2905                2910
Ser Ser Pro Gly Pro Ile Pro Ala Pro Gly Leu Ala Gln Pro Ile Tyr
            2915                2920                2925
Ile Glu Ala Ser Ser Ser His Val Thr Glu Gly Gln Thr Leu Asp Leu
            2930                2935                2940
Asn Cys Val Val Pro Gly Gln Ala His Ala Gln Val Thr Trp Tyr Lys
2945                2950                2955                2960
Arg Gly Gly Ser Leu Pro Ala Arg His Gln Thr His Gly Ser Gln Leu
                2965                2970                2975
Arg Leu His Leu Val Ser Pro Ala Asp Ser Gly Glu Tyr Val Cys Arg
            2980                2985                2990
Ala Ala Ser Gly Pro Gly Pro Glu Gln Glu Ala Ser Phe Thr Val Thr
            2995                3000                3005
Val Pro Pro Ser Glu Gly Ser Ser Tyr Arg Leu Arg Ser Pro Val Ile
            3010                3015                3020
Ser Ile Asp Pro Pro Ser Ser Thr Val Gln Gln Gly Gln Asp Ala Ser
3025                3030                3035                3040
Phe Lys Cys Leu Ile His Asp Gly Ala Ala Pro Ile Ser Leu Glu Trp
                3045                3050                3055
Lys Thr Arg Asn Gln Glu Leu Glu Asp Asn Val His Ile Ser Pro Asn
            3060                3065                3070
Gly Ser Ile Ile Thr Ile Val Gly Thr Arg Pro Ser Asn His Gly Thr
            3075                3080                3085
Tyr Arg Cys Val Ala Ser Asn Ala Tyr Gly Val Ala Gln Ser Val Val
            3090                3095                3100
Asn Leu Ser Val His Gly Pro Pro Thr Val Ser Val Leu Pro Glu Gly
3105                3110                3115                3120
Pro Val Trp Val Lys Val Gly Lys Ala Val Thr Leu Glu Cys Val Ser
                3125                3130                3135
Ala Gly Glu Pro Arg Ser Ser Ala Arg Trp Thr Arg Ile Ser Ser Thr
            3140                3145                3150
Pro Ala Lys Leu Glu Gln Arg Thr Tyr Gly Leu Met Asp Ser His Ala
            3155                3160                3165
Val Leu Gln Ile Ser Ser Ala Lys Pro Ser Asp Ala Gly Thr Tyr Val
            3170                3175                3180
```

```
Cys Leu Ala Gln Asn Ala Leu Gly Thr Ala Gln Lys Gln Val Glu Val
3185                3190                3195                3200

Ile Val Asp Thr Gly Ala Met Ala Pro Gly Ala Pro Gln Val Gln Ala
            3205                3210                3215

Glu Glu Ala Glu Leu Thr Val Glu Ala Gly His Thr Ala Thr Leu Arg
        3220                3225                3230

Cys Ser Ala Thr Gly Ser Pro Ala Pro Thr Ile His Trp Ser Lys Leu
    3235                3240                3245

Arg Ser Pro Leu Pro Trp Gln His Arg Leu Glu Gly Asp Thr Leu Ile
3250                3255                3260

Ile Pro Arg Val Ala Gln Gln Asp Ser Gly Gln Tyr Ile Cys Asn Ala
3265                3270                3275                3280

Thr Ser Pro Ala Gly His Ala Glu Ala Thr Ile Ile Leu His Val Glu
            3285                3290                3295

Ser Pro Pro Tyr Ala Thr Thr Val Pro Glu His Ala Ser Val Gln Ala
            3300                3305                3310

Gly Glu Thr Val Gln Leu Gln Cys Leu Ala His Gly Thr Pro Pro Leu
            3315                3320                3325

Thr Phe Gln Trp Ser Arg Val Gly Ser Ser Leu Pro Gly Arg Ala Thr
    3330                3335                3340

Ala Arg Asn Glu Leu Leu His Phe Glu Arg Ala Ala Pro Glu Asp Ser
3345                3350                3355                3360

Gly Arg Tyr Arg Cys Arg Val Thr Asn Lys Val Gly Ser Ala Glu Ala
            3365                3370                3375

Phe Ala Gln Leu Leu Val Gln Gly Pro Pro Gly Ser Leu Pro Ala Thr
            3380                3385                3390

Ser Ile Pro Ala Gly Ser Thr Pro Thr Val Gln Val Thr Pro Gln Leu
            3395                3400                3405

Glu Thr Lys Ser Ile Gly Ala Ser Val Glu Phe His Cys Ala Val Pro
    3410                3415                3420

Ser Asp Gln Gly Thr Gln Leu Arg Trp Phe Lys Glu Gly Gly Gln Leu
3425                3430                3435                3440

Pro Pro Gly His Ser Val Gln Asp Gly Val Leu Arg Ile Gln Asn Leu
            3445                3450                3455

Asp Gln Ser Cys Gln Gly Thr Tyr Ile Cys Gln Ala His Gly Pro Trp
            3460                3465                3470

Gly Lys Ala Gln Ala Ser Ala Gln Leu Val Ile Gln Ala Leu Pro Ser
    3475                3480                3485

Val Leu Ile Asn Ile Arg Thr Ser Val Gln Thr Val Val Val Gly His
            3490                3495                3500

Ala Val Glu Phe Glu Cys Leu Ala Leu Gly Asp Pro Lys Pro Gln Val
3505                3510                3515                3520

Thr Trp Ser Lys Val Gly Gly His Leu Arg Pro Gly Ile Val Gln Ser
            3525                3530                3535

Gly Gly Val Val Arg Ile Ala His Val Glu Leu Ala Asp Ala Gly Gln
            3540                3545                3550

Tyr Arg Cys Thr Ala Thr Asn Ala Ala Gly Thr Thr Gln Ser His Val
    3555                3560                3565

Leu Leu Leu Val Gln Ala Leu Pro Gln Ile Ser Met Pro Gln Glu Val
        3570                3575                3580

Arg Val Pro Ala Gly Ser Ala Ala Val Phe Pro Cys Ile Ala Ser Gly
3585                3590                3595                3600
```

-continued

```
Tyr Pro Thr Pro Asp Ile Ser Trp Ser Lys Leu Asp Gly Ser Leu Pro
            3605                3610                3615
Pro Asp Ser Arg Leu Glu Asn Asn Met Leu Met Leu Pro Ser Val Arg
        3620                3625                3630
Pro Gln Asp Ala Gly Thr Tyr Val Cys Thr Ala Thr Asn Arg Gln Gly
    3635                3640                3645
Lys Val Lys Ala Phe Ala His Leu Gln Val Pro Glu Arg Val Val Pro
3650                3655                3660
Tyr Phe Thr Gln Thr Pro Tyr Ser Phe Leu Pro Leu Pro Thr Ile Lys
3665                3670                3675                3680
Asp Ala Tyr Arg Lys Phe Glu Ile Lys Ile Thr Phe Arg Pro Asp Ser
            3685                3690                3695
Ala Asp Gly Met Leu Leu Tyr Asn Gly Gln Lys Arg Val Pro Gly Ser
        3700                3705                3710
Pro Thr Asn Leu Ala Asn Arg Gln Pro Asp Phe Ile Ser Phe Gly Leu
    3715                3720                3725
Val Gly Gly Arg Pro Glu Phe Arg Phe Asp Ala Gly Ser Gly Met Ala
    3730                3735                3740
Thr Ile Arg His Pro Thr Pro Leu Ala Leu Gly His Phe His Thr Val
3745                3750                3755                3760
Thr Leu Leu Arg Ser Leu Thr Gln Gly Ser Leu Ile Val Gly Asp Leu
            3765                3770                3775
Ala Pro Val Asn Gly Thr Ser Gln Gly Lys Phe Gln Gly Leu Asp Leu
        3780                3785                3790
Asn Glu Glu Leu Tyr Leu Gly Gly Tyr Pro Asp Tyr Gly Ala Ile Pro
    3795                3800                3805
Lys Ala Gly Leu Ser Ser Gly Phe Ile Gly Cys Val Arg Glu Leu Arg
    3810                3815                3820
Ile Gln Gly Glu Glu Ile Val Phe His Asp Leu Asn Leu Thr Ala His
3825                3830                3835                3840
Gly Ile Ser His Cys Pro Thr Cys Arg Asp Arg Pro Cys Gln Asn Gly
            3845                3850                3855
Gly Gln Cys His Asp Ser Glu Ser Ser Ser Tyr Val Cys Val Cys Pro
        3860                3865                3870
Ala Gly Phe Thr Gly Ser Arg Cys Glu His Ser Gln Ala Leu His Cys
    3875                3880                3885
His Pro Glu Ala Cys Gly Pro Asp Ala Thr Cys Val Asn Arg Pro Asp
    3890                3895                3900
Gly Arg Gly Tyr Thr Cys Arg Cys His Leu Gly Arg Ser Gly Leu Arg
3905                3910                3915                3920
Cys Glu Glu Gly Val Thr Val Thr Thr Pro Ser Leu Ser Gly Ala Gly
            3925                3930                3935
Ser Tyr Leu Ala Leu Pro Ala Leu Thr Asn Thr His His Glu Leu Arg
        3940                3945                3950
Leu Asp Val Glu Phe Lys Pro Leu Ala Pro Asp Gly Val Leu Leu Phe
    3955                3960                3965
Ser Gly Gly Lys Ser Gly Pro Val Glu Asp Phe Val Ser Leu Ala Met
    3970                3975                3980
Val Gly Gly His Leu Glu Phe Arg Tyr Glu Leu Gly Ser Gly Leu Ala
3985                3990                3995                4000
Val Leu Arg Ser Ala Glu Pro Leu Ala Leu Gly Arg Trp His Arg Val
            4005                4010                4015
Ser Ala Glu Arg Leu Asn Lys Asp Gly Ser Leu Arg Val Asn Gly Gly
```

Arg Pro Val Leu Arg Ser Ser Pro Gly Lys Ser Gln Gly Leu Asn Leu
          4020                4025                4030

His Thr Leu Leu Tyr Leu Gly Gly Val Glu Pro Ser Val Pro Leu Ser
     4035                4040                4045

Pro Ala Thr Asn Met Ser Ala His Phe Arg Gly Cys Val Gly Glu Val
4050                4055                4060

Ser Val Asn Gly Lys Arg Leu Asp Leu Thr Tyr Ser Phe Leu Gly Ser
4065                4070                4075                4080

Gln Gly Ile Gly Gln Cys Tyr Asp Ser Ser Pro Cys Glu Arg Gln Pro
               4085                4090                4095

Cys Gln His Gly Ala Thr Cys Met Pro Ala Gly Glu Tyr Glu Phe Gln
     4100                4105                4110

Cys Leu Cys Arg Asp Gly Phe Lys Gly Asp Leu Cys Glu His Glu Glu
     4115                4120                4125

Asn Pro Cys Gln Leu Arg Glu Pro Cys Leu His Gly Gly Thr Cys Gln
     4130                4135                4140

Gly Thr Arg Cys Leu Cys Leu Pro Gly Phe Ser Gly Pro Arg Cys Gln
4145                4150                4155                4160

Gln Gly Ser Gly His Gly Ile Ala Glu Ser Asp Trp His Leu Glu Gly
          4165                4170                4175

Ser Gly Gly Asn Asp Ala Pro Gly Gln Tyr Gly Ala Tyr Phe His Asp
     4180                4185                4190

Asp Gly Phe Leu Ala Phe Pro Gly His Val Phe Ser Arg Ser Leu Pro
     4195                4200                4205

Glu Val Pro Glu Thr Ile Glu Leu Glu Val Arg Thr Ser Thr Ala Ser
     4210                4215                4220

Gly Leu Leu Leu Trp Gln Gly Val Glu Val Gly Glu Ala Gly Gln Gly
4225                4230                4235                4240

Lys Asp Phe Ile Ser Leu Gly Leu Gln Asp Gly His Leu Val Phe Arg
          4245                4250                4255

Tyr Gln Leu Gly Ser Gly Glu Ala Arg Leu Val Ser Glu Asp Pro Ile
     4260                4265                4270

Asn Asp Gly Glu Trp His Arg Val Thr Ala Leu Arg Glu Gly Arg Arg
     4275                4280                4285

Gly Ser Ile Gln Val Asp Gly Glu Glu Leu Val Ser Gly Arg Ser Pro
     4290                4295                4300

Gly Pro Asn Val Ala Val Asn Ala Lys Gly Ser Val Tyr Ile Gly Gly
4305                4310                4315                4320

Ala Pro Asp Val Ala Thr Leu Thr Gly Gly Arg Phe Ser Ser Gly Ile
          4325                4330                4335

Thr Gly Cys Val Lys Asn Leu Val Leu His Ser Ala Arg Pro Gly Ala
     4340                4345                4350

Pro Pro Pro Gln Pro Leu Asp Leu Gln His Arg Ala Gln Ala Gly Ala
     4355                4360                4365

Asn Thr Arg Pro Cys Pro Ser
4370                4375                4380

4385                4390

<210> SEQ ID NO 3
<211> LENGTH: 705
<212> TYPE: PRT
<213> ORGANISM: human

<400> SEQUENCE: 3

-continued

```
Glu Ile Lys Ile Thr Phe Arg Pro Asp Ser Ala Asp Gly Met Leu Leu
 1               5                  10                  15

Tyr Asn Gly Gln Lys Arg Val Pro Gly Ser Pro Thr Asn Leu Ala Asn
             20                  25                  30

Arg Gln Pro Asp Phe Ile Ser Phe Gly Leu Val Gly Gly Arg Pro Glu
         35                  40                  45

Phe Arg Phe Asp Ala Gly Ser Gly Met Ala Thr Ile Arg His Pro Thr
 50                  55                  60

Pro Leu Ala Leu Gly His Phe His Thr Val Thr Leu Leu Arg Ser Leu
 65                  70                  75                  80

Thr Gln Gly Ser Leu Ile Val Gly Asp Leu Ala Pro Val Asn Gly Thr
                 85                  90                  95

Ser Gln Gly Lys Phe Gln Gly Leu Asp Leu Asn Glu Glu Leu Tyr Leu
                100                 105                 110

Gly Gly Tyr Pro Asp Tyr Gly Ala Ile Pro Lys Ala Gly Leu Ser Ser
             115                 120                 125

Gly Phe Ile Gly Cys Val Arg Glu Leu Arg Ile Gln Gly Glu Glu Ile
         130                 135                 140

Val Phe His Asp Leu Asn Leu Thr Ala His Gly Ile Ser His Cys Pro
145                 150                 155                 160

Thr Cys Arg Asp Arg Pro Cys Gln Asn Gly Gly Gln Cys His Asp Ser
                165                 170                 175

Glu Ser Ser Ser Tyr Val Cys Val Cys Pro Ala Gly Phe Thr Gly Ser
                180                 185                 190

Arg Cys Glu His Ser Gln Ala Leu His Cys His Pro Glu Ala Cys Gly
    195                 200                 205

Pro Asp Ala Thr Cys Val Asn Arg Pro Asp Gly Arg Gly Tyr Thr Cys
210                 215                 220

Arg Cys His Leu Gly Arg Ser Gly Leu Arg Cys Glu Glu Gly Val Thr
225                 230                 235                 240

Val Thr Thr Pro Ser Leu Ser Gly Ala Gly Ser Tyr Leu Ala Leu Pro
                245                 250                 255

Ala Leu Thr Asn Thr His His Glu Leu Arg Leu Asp Val Glu Phe Lys
                260                 265                 270

Pro Leu Ala Pro Asp Gly Val Leu Leu Phe Ser Gly Gly Lys Ser Gly
             275                 280                 285

Pro Val Glu Asp Phe Val Ser Leu Ala Met Val Gly Gly His Leu Glu
         290                 295                 300

Phe Arg Tyr Glu Leu Gly Ser Gly Leu Ala Val Leu Arg Ser Ala Glu
305                 310                 315                 320

Pro Leu Ala Leu Gly Arg Trp His Arg Val Ser Ala Glu Arg Leu Asn
                325                 330                 335

Lys Asp Gly Ser Leu Arg Val Asn Gly Gly Arg Pro Val Leu Arg Ser
             340                 345                 350

Ser Pro Gly Lys Ser Gln Gly Leu Asn Leu His Thr Leu Leu Tyr Leu
         355                 360                 365

Gly Gly Val Glu Pro Ser Val Pro Leu Ser Pro Ala Thr Asn Met Ser
     370                 375                 380

Ala His Phe Arg Gly Cys Val Gly Glu Val Ser Val Asn Gly Lys Arg
385                 390                 395                 400

Leu Asp Leu Thr Tyr Ser Phe Leu Gly Ser Gln Gly Ile Gly Gln Cys
                405                 410                 415

Tyr Asp Ser Ser Pro Cys Glu Arg Gln Pro Cys Gln His Gly Ala Thr
```

-continued

```
            420             425             430
Cys Met Pro Ala Gly Glu Tyr Glu Phe Gln Cys Leu Cys Arg Asp Gly
        435                 440                 445
Phe Lys Gly Asp Leu Cys Glu His Glu Glu Asn Pro Cys Gln Leu Arg
    450                 455                 460
Glu Pro Cys Leu His Gly Thr Cys Gln Gly Thr Arg Cys Leu Cys
465                 470                 475                 480
Leu Pro Gly Phe Ser Gly Pro Arg Cys Gln Gln Gly Ser Gly His Gly
                485                 490                 495
Ile Ala Glu Ser Asp Trp His Leu Glu Gly Ser Gly Gly Asn Asp Ala
            500                 505                 510
Pro Gly Gln Tyr Gly Ala Tyr Phe His Asp Asp Gly Phe Leu Ala Phe
        515                 520                 525
Pro Gly His Val Phe Ser Arg Ser Leu Pro Glu Val Pro Glu Thr Ile
    530                 535                 540
Glu Leu Glu Val Arg Thr Ser Thr Ala Ser Gly Leu Leu Leu Trp Gln
545                 550                 555                 560
Gly Val Glu Val Gly Glu Ala Gly Gln Gly Lys Asp Phe Ile Ser Leu
                565                 570                 575
Gly Leu Gln Asp Gly His Leu Val Phe Arg Tyr Gln Leu Gly Ser Gly
            580                 585                 590
Glu Ala Arg Leu Val Ser Glu Asp Pro Ile Asn Asp Gly Glu Trp His
        595                 600                 605
Arg Val Thr Ala Leu Arg Glu Gly Arg Gly Ser Ile Gln Val Asp
    610                 615                 620
Gly Glu Glu Leu Val Ser Gly Arg Ser Pro Gly Pro Asn Val Ala Val
625                 630                 635                 640
Asn Ala Lys Gly Ser Val Tyr Ile Gly Gly Ala Pro Asp Val Ala Thr
                645                 650                 655
Leu Thr Gly Gly Arg Phe Ser Ser Gly Ile Thr Gly Cys Val Lys Asn
            660                 665                 670
Leu Val Leu His Ser Ala Arg Pro Gly Ala Pro Pro Gln Pro Leu
        675                 680                 685
Asp Leu Gln His Arg Ala Gln Ala Gly Ala Asn Thr Arg Pro Cys Pro
    690                 695                 700
Ser
705

<210> SEQ ID NO 4
<211> LENGTH: 495
<212> TYPE: PRT
<213> ORGANISM: human

<400> SEQUENCE: 4

Glu Ile Lys Ile Thr Phe Arg Pro Asp Ser Ala Asp Gly Met Leu Leu
  1               5                  10                  15
Tyr Asn Gly Gln Lys Arg Val Pro Gly Ser Pro Thr Asn Leu Ala Asn
            20                  25                  30
Arg Gln Pro Asp Phe Ile Ser Phe Gly Leu Val Gly Gly Arg Pro Glu
        35                  40                  45
Phe Arg Phe Asp Ala Gly Ser Gly Met Ala Thr Ile Arg His Pro Thr
    50                  55                  60
Pro Leu Ala Leu Gly His Phe His Thr Val Thr Leu Leu Arg Ser Leu
65                  70                  75                  80
```

-continued

```
Thr Gln Gly Ser Leu Ile Val Gly Asp Leu Ala Pro Val Asn Gly Thr
                85                  90                  95
Ser Gln Gly Lys Phe Gln Gly Leu Asp Leu Asn Glu Glu Leu Tyr Leu
            100                 105                 110
Gly Gly Tyr Pro Asp Tyr Gly Ala Ile Pro Lys Ala Gly Leu Ser Ser
            115                 120                 125
Gly Phe Ile Gly Cys Val Arg Glu Leu Arg Ile Gln Gly Glu Glu Ile
    130                 135                 140
Val Phe His Asp Leu Asn Leu Thr Ala His Gly Ile Ser His Cys Pro
145                 150                 155                 160
Thr Cys Arg Asp Arg Pro Cys Gln Asn Gly Gly Gln Cys His Asp Ser
                165                 170                 175
Glu Ser Ser Tyr Val Cys Val Cys Pro Ala Gly Phe Thr Gly Ser
            180                 185                 190
Arg Cys Glu His Ser Gln Ala Leu His Cys His Pro Glu Ala Cys Gly
            195                 200                 205
Pro Asp Ala Thr Cys Val Asn Arg Pro Asp Gly Arg Gly Tyr Thr Cys
    210                 215                 220
Arg Cys His Leu Gly Arg Ser Gly Leu Arg Cys Glu Glu Gly Val Thr
225                 230                 235                 240
Val Thr Thr Pro Ser Leu Ser Gly Ala Gly Ser Tyr Leu Ala Leu Pro
                245                 250                 255
Ala Leu Thr Asn Thr His His Glu Leu Arg Leu Asp Val Glu Phe Lys
            260                 265                 270
Pro Leu Ala Pro Asp Gly Val Leu Leu Phe Ser Gly Gly Lys Ser Gly
            275                 280                 285
Pro Val Glu Asp Phe Val Ser Leu Ala Met Val Gly Gly His Leu Glu
    290                 295                 300
Phe Arg Tyr Glu Leu Gly Ser Gly Leu Ala Val Leu Arg Ser Ala Glu
305                 310                 315                 320
Pro Leu Ala Leu Gly Arg Trp His Arg Val Ser Ala Glu Arg Leu Asn
                325                 330                 335
Lys Asp Gly Ser Leu Arg Val Asn Gly Gly Arg Pro Val Leu Arg Ser
            340                 345                 350
Ser Pro Gly Lys Ser Gln Gly Leu Asn Leu His Thr Leu Leu Tyr Leu
            355                 360                 365
Gly Gly Val Glu Pro Ser Val Pro Leu Ser Pro Ala Thr Asn Met Ser
    370                 375                 380
Ala His Phe Arg Gly Cys Val Gly Glu Val Ser Val Asn Gly Lys Arg
385                 390                 395                 400
Leu Asp Leu Thr Tyr Ser Phe Leu Gly Ser Gln Gly Ile Gly Gln Cys
                405                 410                 415
Tyr Asp Ser Ser Pro Cys Glu Arg Gln Pro Cys Gln His Gly Ala Thr
            420                 425                 430
Cys Met Pro Ala Gly Glu Tyr Glu Phe Gln Cys Leu Cys Arg Asp Gly
    435                 440                 445
Phe Lys Gly Asp Leu Cys Glu His Glu Glu Asn Pro Cys Gln Leu Arg
450                 455                 460
Glu Pro Cys Leu His Gly Gly Thr Cys Gln Gly Thr Arg Cys Leu Cys
465                 470                 475                 480
Leu Pro Gly Phe Ser Gly Pro Arg Cys Gln Gln Gly Ser Gly His
                485                 490                 495
```

```
<210> SEQ ID NO 5
<211> LENGTH: 240
<212> TYPE: PRT
<213> ORGANISM: human

<400> SEQUENCE: 5

Glu Ile Lys Ile Thr Phe Arg Pro Asp Ser Ala Asp Gly Met Leu Leu
 1               5                  10                  15

Tyr Asn Gly Gln Lys Arg Val Pro Gly Ser Pro Thr Asn Leu Ala Asn
                20                  25                  30

Arg Gln Pro Asp Phe Ile Ser Phe Gly Leu Val Gly Gly Arg Pro Glu
            35                  40                  45

Phe Arg Phe Asp Ala Gly Ser Gly Met Ala Thr Ile Arg His Pro Thr
 50                  55                  60

Pro Leu Ala Leu Gly His Phe His Thr Val Thr Leu Leu Arg Ser Leu
 65                  70                  75                  80

Thr Gln Gly Ser Leu Ile Val Gly Asp Leu Ala Pro Val Asn Gly Thr
                85                  90                  95

Ser Gln Gly Lys Phe Gln Gly Leu Asp Leu Asn Glu Glu Leu Tyr Leu
            100                 105                 110

Gly Gly Tyr Pro Asp Tyr Gly Ala Ile Pro Lys Ala Gly Leu Ser Ser
        115                 120                 125

Gly Phe Ile Gly Cys Val Arg Glu Leu Arg Ile Gln Gly Glu Glu Ile
    130                 135                 140

Val Phe His Asp Leu Asn Leu Thr Ala His Gly Ile Ser His Cys Pro
145                 150                 155                 160

Thr Cys Arg Asp Arg Pro Cys Gln Asn Gly Gly Gln Cys His Asp Ser
                165                 170                 175

Glu Ser Ser Ser Tyr Val Cys Val Cys Pro Ala Gly Phe Thr Gly Ser
            180                 185                 190

Arg Cys Glu His Ser Gln Ala Leu His Cys His Pro Glu Ala Cys Gly
        195                 200                 205

Pro Asp Ala Thr Cys Val Asn Arg Pro Asp Gly Arg Gly Tyr Thr Cys
    210                 215                 220

Arg Cys His Leu Gly Arg Ser Gly Leu Arg Cys Glu Glu Gly Val Thr
225                 230                 235                 240

<210> SEQ ID NO 6
<211> LENGTH: 161
<212> TYPE: PRT
<213> ORGANISM: human

<400> SEQUENCE: 6

Glu Ile Lys Ile Thr Phe Arg Pro Asp Ser Ala Asp Gly Met Leu Leu
 1               5                  10                  15

Tyr Asn Gly Gln Lys Arg Val Pro Gly Ser Pro Thr Asn Leu Ala Asn
                20                  25                  30

Arg Gln Pro Asp Phe Ile Ser Phe Gly Leu Val Gly Gly Arg Pro Glu
            35                  40                  45

Phe Arg Phe Asp Ala Gly Ser Gly Met Ala Thr Ile Arg His Pro Thr
 50                  55                  60

Pro Leu Ala Leu Gly His Phe His Thr Val Thr Leu Leu Arg Ser Leu
 65                  70                  75                  80

Thr Gln Gly Ser Leu Ile Val Gly Asp Leu Ala Pro Val Asn Gly Thr
                85                  90                  95

Ser Gln Gly Lys Phe Gln Gly Leu Asp Leu Asn Glu Glu Leu Tyr Leu
```

-continued

```
                100                 105                 110
Gly Gly Tyr Pro Asp Tyr Gly Ala Ile Pro Lys Ala Gly Leu Ser Ser
            115                 120                 125

Gly Phe Ile Gly Cys Val Arg Glu Leu Arg Ile Gln Gly Glu Glu Ile
        130                 135                 140

Val Phe His Asp Leu Asn Leu Thr Ala His Gly Ile Ser His Cys Pro
145                 150                 155                 160

Thr

<210> SEQ ID NO 7
<211> LENGTH: 79
<212> TYPE: PRT
<213> ORGANISM: human

<400> SEQUENCE: 7

Cys Arg Asp Arg Pro Cys Gln Asn Gly Gly Gln Cys His Asp Ser Glu
1               5                   10                  15

Ser Ser Ser Tyr Val Cys Val Cys Pro Ala Gly Phe Thr Gly Ser Arg
            20                  25                  30

Cys Glu His Ser Gln Ala Leu His Cys His Pro Glu Ala Cys Gly Pro
        35                  40                  45

Asp Ala Thr Cys Val Asn Arg Pro Asp Gly Arg Gly Tyr Thr Cys Arg
    50                  55                  60

Cys His Leu Gly Arg Ser Gly Leu Arg Cys Glu Glu Gly Val Thr
65                  70                  75

<210> SEQ ID NO 8
<211> LENGTH: 255
<212> TYPE: PRT
<213> ORGANISM: human

<400> SEQUENCE: 8

Val Thr Thr Pro Ser Leu Ser Gly Ala Gly Ser Tyr Leu Ala Leu Pro
1               5                   10                  15

Ala Leu Thr Asn Thr His His Glu Leu Arg Leu Asp Val Glu Phe Lys
            20                  25                  30

Pro Leu Ala Pro Asp Gly Val Leu Leu Phe Ser Gly Gly Lys Ser Gly
            35                  40                  45
]
Pro Val Glu Asp Phe Val Ser Leu Ala Met Val Gly Gly His Leu Glu
    50                  55                  60

Phe Arg Tyr Glu Leu Gly Ser Gly Leu Ala Val Leu Arg Ser Ala Glu
65                  70                  75                  80

Pro Leu Ala Leu Gly Arg Trp His Arg Val Ser Ala Glu Arg Leu Asn
            85                  90                  95

Lys Asp Gly Ser Leu Arg Val Asn Gly Gly Arg Pro Val Leu Arg Ser
            100                 105                 110

Ser Pro Gly Lys Ser Gln Gly Leu Asn Leu His Thr Leu Leu Tyr Leu
        115                 120                 125

Gly Gly Val Glu Pro Ser Val Pro Leu Ser Pro Ala Thr Asn Met Ser
    130                 135                 140

Ala His Phe Arg Gly Cys Val Gly Glu Val Ser Val Asn Gly Lys Arg
145                 150                 155                 160

Leu Asp Leu Thr Tyr Ser Phe Leu Gly Ser Gln Gly Ile Gly Gln Cys
            165                 170                 175

Tyr Asp Ser Ser Pro Cys Glu Arg Gln Pro Cys Gln His Gly Ala Thr
            180                 185                 190
```

```
Cys Met Pro Ala Gly Glu Tyr Glu Phe Gln Cys Leu Cys Arg Asp Gly
            195                 200                 205

Phe Lys Gly Asp Leu Cys Glu His Glu Glu Asn Pro Cys Gln Leu Arg
        210                 215                 220

Glu Pro Cys Leu His Gly Gly Thr Cys Gln Gly Thr Arg Cys Leu Cys
225                 230                 235                 240

Leu Pro Gly Phe Ser Gly Pro Arg Cys Gln Gln Gly Ser Gly His
                245                 250                 255

<210> SEQ ID NO 9
<211> LENGTH: 284
<212> TYPE: PRT
<213> ORGANISM: human

<400> SEQUENCE: 9

Cys Glu Arg Gln Pro Cys Gln His Gly Ala Thr Cys Met Pro Ala Gly
1               5                   10                  15

Glu Tyr Glu Phe Gln Cys Leu Cys Arg Asp Gly Phe Lys Gly Asp Leu
            20                  25                  30

Cys Glu His Glu Glu Asn Pro Cys Gln Leu Arg Glu Pro Cys Leu His
        35                  40                  45

Gly Gly Thr Cys Gln Gly Thr Arg Cys Leu Cys Leu Pro Gly Phe Ser
    50                  55                  60

Gly Pro Arg Cys Gln Gln Gly Ser Gly His Gly Ile Ala Glu Ser Asp
65                  70                  75                  80

Trp His Leu Glu Gly Ser Gly Asn Asp Ala Pro Gly Gln Tyr Gly
                85                  90                  95

Ala Tyr Phe His Asp Asp Gly Phe Leu Ala Phe Pro Gly His Val Phe
            100                 105                 110

Ser Arg Ser Leu Pro Glu Val Pro Glu Thr Ile Glu Leu Glu Val Arg
        115                 120                 125

Thr Ser Thr Ala Ser Gly Leu Leu Leu Trp Gln Gly Val Glu Val Gly
    130                 135                 140

Glu Ala Gly Gln Gly Lys Asp Phe Ile Ser Leu Gly Leu Gln Asp Gly
145                 150                 155                 160

His Leu Val Phe Arg Tyr Gln Leu Gly Ser Gly Glu Ala Arg Leu Val
                165                 170                 175

Ser Glu Asp Pro Ile Asn Asp Gly Glu Trp His Arg Val Thr Ala Leu
            180                 185                 190

Arg Glu Gly Arg Arg Gly Ser Ile Gln Val Asp Gly Glu Glu Leu Val
        195                 200                 205

Ser Gly Arg Ser Pro Gly Pro Asn Val Ala Val Asn Ala Lys Gly Ser
    210                 215                 220

Val Tyr Ile Gly Gly Ala Pro Asp Val Ala Thr Leu Thr Gly Gly Arg
225                 230                 235                 240

Phe Ser Ser Gly Ile Thr Gly Cys Val Lys Asn Leu Val Leu His Ser
                245                 250                 255

Ala Arg Pro Gly Ala Pro Pro Gln Pro Leu Asp Leu Gln His Arg
            260                 265                 270

Ala Gln Ala Gly Ala Asn Thr Arg Pro Cys Pro Ser
        275                 280

<210> SEQ ID NO 10
<211> LENGTH: 210
<212> TYPE: PRT
```

<213> ORGANISM: human

<400> SEQUENCE: 10

```
Gly Ile Ala Glu Ser Asp Trp His Leu Glu Gly Ser Gly Gly Asn Asp
 1               5                  10                  15
Ala Pro Gly Gln Tyr Gly Ala Tyr Phe His Asp Asp Gly Phe Leu Ala
                20                  25                  30
Phe Pro Gly His Val Phe Ser Arg Ser Leu Pro Glu Val Pro Glu Thr
            35                  40                  45
Ile Glu Leu Glu Val Arg Thr Ser Thr Ala Ser Gly Leu Leu Leu Trp
        50                  55                  60
Gln Gly Val Glu Val Gly Glu Ala Gly Gln Gly Lys Asp Phe Ile Ser
65                  70                  75                  80
Leu Gly Leu Gln Asp Gly His Leu Val Phe Arg Tyr Gln Leu Gly Ser
                85                  90                  95
Gly Glu Ala Arg Leu Val Ser Glu Asp Pro Ile Asn Asp Gly Glu Trp
            100                 105                 110
His Arg Val Thr Ala Leu Arg Glu Gly Arg Arg Gly Ser Ile Gln Val
        115                 120                 125
Asp Gly Glu Glu Leu Val Ser Gly Arg Ser Pro Gly Pro Asn Val Ala
    130                 135                 140
Val Asn Ala Lys Gly Ser Val Tyr Ile Gly Gly Ala Pro Asp Val Ala
145                 150                 155                 160
Thr Leu Thr Gly Gly Arg Phe Ser Ser Gly Ile Thr Gly Cys Val Lys
                165                 170                 175
Asn Leu Val Leu His Ser Ala Arg Pro Gly Ala Pro Pro Gln Pro
            180                 185                 190
Leu Asp Leu Gln His Arg Ala Gln Ala Gly Ala Asn Thr Arg Pro Cys
        195                 200                 205
Pro Ser
    210
```